United States Patent
Waycuilis et al.

(10) Patent No.: US 9,193,641 B2
(45) Date of Patent: Nov. 24, 2015

(54) PROCESSES AND SYSTEMS FOR CONVERSION OF ALKYL BROMIDES TO HIGHER MOLECULAR WEIGHT HYDROCARBONS IN CIRCULATING CATALYST REACTOR-REGENERATOR SYSTEMS

(71) Applicant: GTC Technology US, LLC, Houston, TX (US)

(72) Inventors: John J. Waycuilis, Cypress, TX (US); Raphael Thomas, Houston, TX (US); Patrick K. Moore, Houston, TX (US)

(73) Assignee: GTC Technology US, LLC, Houston, TX (US)

( * ) Notice: Subject to any disclaimer, the term of this patent is extended or adjusted under 35 U.S.C. 154(b) by 0 days.

(21) Appl. No.: 13/705,106

(22) Filed: Dec. 4, 2012

(65) Prior Publication Data
US 2013/0158324 A1     Jun. 20, 2013

Related U.S. Application Data

(60) Provisional application No. 61/576,918, filed on Dec. 16, 2011.

(51) Int. Cl.
C07C 1/30 (2006.01)
C07C 1/32 (2006.01)

(52) U.S. Cl.
CPC . *C07C 1/321* (2013.01); *C07C 1/30* (2013.01); *C07C 2529/06* (2013.01)

(58) Field of Classification Search
None
See application file for complete search history.

(56) References Cited

U.S. PATENT DOCUMENTS

| 2,168,260 | A | 8/1939 | Heisel et al. |
| 2,246,082 | A | 6/1941 | Vaughan et al. |
| 2,320,257 | A | 5/1943 | Beekhuis |
| 2,488,083 | A | 11/1949 | Gorin et al. |

(Continued)

FOREIGN PATENT DOCUMENTS

| CA | 1099656 | 4/1981 |
| CA | 1101441 | 5/1981 |

(Continued)

OTHER PUBLICATIONS

U.S. Office Communication from U.S. Appl. No. 10/365,346 dated June. 12, 2006.

(Continued)

*Primary Examiner* — Tam M Nguyen
(74) *Attorney, Agent, or Firm* — Tumey L.L.P.

(57) ABSTRACT

Process and system that include the conversion of alkyl bromides to higher molecular weight hydrocarbons in circulating catalyst reactor-regenerator systems. Alkyl bromides may be reacted over a catalyst in at least one conversion reactor to produce at least an effluent stream comprising higher molecular weight hydrocarbons and hydrogen bromide. A portion of the catalyst may be removed from the conversion reactor. The portion of the catalyst may be contacted with a stripping gas to displace hydrocarbons from the portion of the catalyst. The portion of the catalyst may be contacted a first inert gas. The portion of the catalyst may be contacted with oxygen to form a regenerated catalyst by removal of coke. The regenerated catalyst may be contacted with a second inert gas. At least a portion of the regenerated catalyst may be introduced into the conversion reactor.

19 Claims, 5 Drawing Sheets

(56) References Cited

U.S. PATENT DOCUMENTS

| | | |
|---|---|---|
| 2,536,457 A | 1/1951 | Mugdan |
| 2,666,024 A | 1/1954 | Low et al. |
| 2,677,598 A | 5/1954 | Crummett et al. |
| 2,809,930 A | 10/1957 | Miller |
| 2,941,014 A | 6/1960 | Rothweiler et al. |
| 3,076,784 A | 2/1963 | Schulte-Huemann et al. |
| 3,172,915 A | 3/1965 | Borkowski et al. |
| 3,181,934 A | 5/1965 | Davis |
| 3,233,972 A | 2/1966 | Walker et al. |
| 3,240,564 A | 3/1966 | Uffelmann et al. |
| 3,246,043 A | 4/1966 | Rosset et al. |
| 3,254,023 A | 5/1966 | Miale et al. |
| 3,273,964 A | 9/1966 | Rosset |
| 3,291,708 A | 12/1966 | Juda |
| 3,294,846 A | 12/1966 | Livak et al. |
| 3,310,380 A | 3/1967 | Lester |
| 3,314,762 A | 4/1967 | Hahn |
| 3,346,340 A | 10/1967 | Louvar et al. |
| 3,353,916 A | 11/1967 | Lester |
| 3,353,919 A | 11/1967 | Stockman |
| 3,379,506 A | 4/1968 | Massonne et al. |
| 3,468,968 A | 9/1969 | Baker et al. |
| 3,496,242 A | 2/1970 | Berkowitz et al. |
| 3,562,321 A | 2/1971 | Borkowski et al. |
| 3,598,876 A | 8/1971 | Bloch |
| 3,615,265 A | 10/1971 | Gartner |
| 3,642,447 A | 2/1972 | Hahn et al. |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,927,111 A | 12/1975 | Robinson |
| 3,928,483 A | 12/1975 | Chang et al. |
| 3,959,450 A | 5/1976 | Calloue et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,819 A | 9/1977 | Schmerling |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,379,734 A | 4/1983 | Franzen |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |

(56) References Cited

U.S. PATENT DOCUMENTS

| | | |
|---|---|---|
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,626,607 A | 12/1986 | Jacquinot et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,725,425 A | 2/1988 | Lesher et al. |
| 4,735,747 A | 4/1988 | Ollivier et al. |
| 4,737,594 A | 4/1988 | Olah |
| 4,748,013 A | 5/1988 | Saito et al. |
| 4,762,596 A | 8/1988 | Huang et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaeding |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,939,314 A | 7/1990 | Harandi et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |
| 4,973,776 A | 11/1990 | Allenger et al. |
| 4,973,786 A | 11/1990 | Karra |
| 4,982,024 A | 1/1991 | Lin et al. |
| 4,982,041 A | 1/1991 | Campbell |
| 4,988,660 A | 1/1991 | Campbell |
| 4,990,696 A | 2/1991 | Stauffer |
| 4,990,711 A | 2/1991 | Chen et al. |
| 5,001,293 A | 3/1991 | Nubel et al. |
| 5,004,847 A | 4/1991 | Beaver et al. |
| 5,013,424 A | 5/1991 | James, Jr. et al. |
| 5,013,793 A | 5/1991 | Wang et al. |
| 5,019,652 A | 5/1991 | Taylor et al. |
| 5,026,934 A | 6/1991 | Bains et al. |
| 5,026,937 A | 6/1991 | Bricker |
| 5,026,944 A | 6/1991 | Allenger et al. |
| 5,034,566 A | 7/1991 | Ishino et al. |
| 5,043,502 A | 8/1991 | Martindale et al. |
| 5,055,235 A | 10/1991 | Brackenridge et al. |
| 5,055,625 A | 10/1991 | Neidiffer et al. |
| 5,055,633 A | 10/1991 | Volles |
| 5,055,634 A | 10/1991 | Volles |
| 5,059,744 A | 10/1991 | Harandi et al. |
| 5,068,478 A | 11/1991 | Miller et al. |
| 5,071,449 A | 12/1991 | Sircar |
| 5,071,815 A | 12/1991 | Wallace et al. |
| 5,073,656 A | 12/1991 | Chafin et al. |
| 5,073,657 A | 12/1991 | Warren |
| 5,082,473 A | 1/1992 | Keefer |
| 5,082,816 A | 1/1992 | Teller et al. |
| 5,085,674 A | 2/1992 | Leavitt |
| 5,087,779 A | 2/1992 | Nubel et al. |
| 5,087,786 A | 2/1992 | Nubel et al. |
| 5,087,787 A | 2/1992 | Kimble et al. |
| 5,093,533 A | 3/1992 | Wilson |
| 5,093,542 A | 3/1992 | Gaffney |
| 5,096,469 A | 3/1992 | Keefer |
| 5,097,083 A | 3/1992 | Stauffer |
| 5,099,084 A | 3/1992 | Stauffer |
| 5,105,045 A | 4/1992 | Kimble et al. |
| 5,105,046 A | 4/1992 | Washecheck |
| 5,107,032 A | 4/1992 | Erb et al. |
| 5,107,051 A | 4/1992 | Pannell |
| 5,107,061 A | 4/1992 | Ou et al. |
| 5,108,579 A | 4/1992 | Casci |
| 5,118,899 A | 6/1992 | Kimble et al. |
| 5,120,332 A | 6/1992 | Wells |
| 5,132,343 A | 7/1992 | Zwecker et al. |
| 5,138,112 A | 8/1992 | Gosling et al. |
| 5,139,991 A | 8/1992 | Taylor et al. |
| 5,146,027 A | 9/1992 | Gaffney |
| 5,157,189 A | 10/1992 | Karra |
| 5,160,502 A | 11/1992 | Kimble et al. |
| 5,166,452 A | 11/1992 | Gradl et al. |
| 5,175,382 A | 12/1992 | Hebgen et al. |
| 5,178,748 A | 1/1993 | Casci et al. |
| 5,185,479 A | 2/1993 | Stauffer |
| 5,188,725 A | 2/1993 | Harandi |
| 5,191,142 A | 3/1993 | Marshall et al. |
| 5,194,244 A | 3/1993 | Brownscombe et al. |
| 5,202,506 A | 4/1993 | Kirchner et al. |
| 5,202,511 A | 4/1993 | Salinas, III et al. |
| 5,208,402 A | 5/1993 | Wilson |
| 5,210,357 A | 5/1993 | Kolts et al. |
| 5,215,648 A | 6/1993 | Zones et al. |
| 5,223,471 A | 6/1993 | Washecheck |
| 5,228,888 A | 7/1993 | Gmelin et al. |
| 5,233,113 A | 8/1993 | Periana et al. |
| 5,237,115 A | 8/1993 | Makovec et al. |

(56) References Cited

U.S. PATENT DOCUMENTS

| | | |
|---|---|---|
| 5,243,098 A | 9/1993 | Miller et al. |
| 5,243,114 A | 9/1993 | Johnson et al. |
| 5,245,109 A | 9/1993 | Kaminsky et al. |
| 5,254,772 A | 10/1993 | Dukat et al. |
| 5,254,790 A | 10/1993 | Thomas et al. |
| 5,264,635 A | 11/1993 | Le et al. |
| 5,268,518 A | 12/1993 | West et al. |
| 5,276,226 A | 1/1994 | Horvath et al. |
| 5,276,240 A | 1/1994 | Timmons et al. |
| 5,276,242 A | 1/1994 | Wu |
| 5,284,990 A | 2/1994 | Peterson et al. |
| 5,300,126 A | 4/1994 | Brown et al. |
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,358,645 A | 10/1994 | Hong et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A | 1/1995 | Howarth et al. |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |
| 5,401,894 A | 3/1995 | Brasier et al. |
| 5,406,017 A | 4/1995 | Withers, Jr. |
| 5,411,641 A | 5/1995 | Trainham, III et al. |
| 5,414,173 A | 5/1995 | Garces et al. |
| 5,430,210 A | 7/1995 | Grasselli et al. |
| 5,430,214 A | 7/1995 | Smith et al. |
| 5,430,219 A | 7/1995 | Sanfilippo et al. |
| 5,433,828 A | 7/1995 | van Velzen et al. |
| 5,436,378 A | 7/1995 | Masini et al. |
| 5,444,168 A | 8/1995 | Brown |
| 5,446,234 A | 8/1995 | Casci et al. |
| 5,453,557 A | 9/1995 | Harley et al. |
| 5,456,822 A | 10/1995 | Marcilly et al. |
| 5,457,255 A | 10/1995 | Kumata et al. |
| 5,464,799 A | 11/1995 | Casci et al. |
| 5,465,699 A | 11/1995 | Voigt |
| 5,470,377 A | 11/1995 | Whitlock |
| 5,480,629 A | 1/1996 | Thompson et al. |
| 5,486,627 A | 1/1996 | Quarderer, Jr. et al. |
| 5,489,719 A | 2/1996 | Le et al. |
| 5,489,727 A | 2/1996 | Randolph et al. |
| 5,500,297 A | 3/1996 | Thompson et al. |
| 5,510,525 A | 4/1996 | Sen et al. |
| 5,523,503 A | 6/1996 | Funk et al. |
| 5,525,230 A | 6/1996 | Wrigley et al. |
| 5,538,540 A | 7/1996 | Whitlock |
| 5,563,313 A | 10/1996 | Chung et al. |
| 5,565,092 A | 10/1996 | Pannell et al. |
| 5,565,616 A | 10/1996 | Li et al. |
| 5,571,762 A | 11/1996 | Clerici et al. |
| 5,571,885 A | 11/1996 | Chung et al. |
| 5,599,381 A | 2/1997 | Whitlock |
| 5,600,043 A | 2/1997 | Johnston et al. |
| 5,600,045 A | 2/1997 | Van Der Aalst et al. |
| 5,609,654 A | 3/1997 | Le et al. |
| 5,633,419 A | 5/1997 | Spencer et al. |
| 5,639,930 A | 6/1997 | Penick |
| 5,653,956 A | 8/1997 | Zones |
| 5,656,149 A | 8/1997 | Zones et al. |
| 5,661,097 A | 8/1997 | Spencer et al. |
| 5,663,465 A | 9/1997 | Clegg et al. |
| 5,663,474 A | 9/1997 | Pham et al. |
| 5,674,464 A | 10/1997 | Van Velzen et al. |
| 5,675,046 A | 10/1997 | Ohno et al. |
| 5,675,052 A | 10/1997 | Menon et al. |
| 5,679,134 A | 10/1997 | Brugerolle et al. |
| 5,679,879 A | 10/1997 | Mercier et al. |
| 5,684,213 A | 11/1997 | Nemphos et al. |
| 5,693,191 A | 12/1997 | Pividal et al. |
| 5,695,890 A | 12/1997 | Thompson et al. |
| 5,698,747 A | 12/1997 | Godwin et al. |
| 5,705,712 A | 1/1998 | Frey et al. |
| 5,705,728 A | 1/1998 | Viswanathan et al. |
| 5,705,729 A | 1/1998 | Huang |
| 5,708,246 A | 1/1998 | Camaioni et al. |
| 5,720,858 A | 2/1998 | Noceti et al. |
| 5,728,897 A | 3/1998 | Buysch et al. |
| 5,728,905 A | 3/1998 | Clegg et al. |
| 5,734,073 A | 3/1998 | Chambers et al. |
| 5,741,949 A | 4/1998 | Mack |
| 5,744,669 A | 4/1998 | Kalnes et al. |
| 5,750,801 A | 5/1998 | Buysch et al. |
| 5,770,175 A | 6/1998 | Zones |
| 5,776,871 A | 7/1998 | Cothran et al. |
| 5,780,703 A | 7/1998 | Chang et al. |
| 5,782,936 A | 7/1998 | Riley |
| 5,798,314 A | 8/1998 | Spencer et al. |
| 5,814,715 A | 9/1998 | Chen et al. |
| 5,817,904 A | 10/1998 | Vic et al. |
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,882,614 A | 3/1999 | Taylor, Jr. et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,928,488 A | 7/1999 | Newman |
| 5,952,538 A | 9/1999 | Vaughn et al. |
| 5,959,170 A | 9/1999 | Withers, Jr. et al. |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller et al. |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,093,306 A | 7/2000 | Hanrahan et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson et al. |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |

(56) References Cited

U.S. PATENT DOCUMENTS

| | | | |
|---|---|---|---|
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,491,809 B1 | 12/2002 | Briot et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,627,777 B2 | 9/2003 | Rossi et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 | 10/2005 | Yan et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,111 B1 | 5/2006 | DeGroot et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |

(56) References Cited

U.S. PATENT DOCUMENTS

| | | |
|---|---|---|
| 7,282,603 B2 | 10/2007 | Richards |
| 7,285,698 B2 | 10/2007 | Liu et al. |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,365,102 B1 | 4/2008 | Weissman |
| 7,390,395 B2 | 6/2008 | Elomari |
| 7,560,607 B2 | 7/2009 | Waycuilis |
| 7,674,941 B2 | 3/2010 | Waycuilis et al. |
| 7,713,510 B2 | 5/2010 | Harrod et al. |
| 8,008,535 B2 | 8/2011 | Waycuilis |
| 8,173,851 B2 | 5/2012 | Waycuilis et al. |
| 8,198,495 B2 | 6/2012 | Waycuilis et al. |
| 8,232,441 B2 | 7/2012 | Waycuilis |
| 8,282,810 B2 | 10/2012 | Waycuilis |
| 8,367,884 B2 | 2/2013 | Waycuilis |
| 8,373,015 B2 | 2/2013 | Stark et al. |
| 8,415,517 B2 | 4/2013 | Gadewar et al. |
| 8,436,220 B2 | 5/2013 | Kurukchi et al. |
| 8,449,849 B2 | 5/2013 | Gadewar et al. |
| 8,642,822 B2 | 2/2014 | Brickey et al. |
| 2001/0051662 A1 | 12/2001 | Arcuri et al. |
| 2002/0102672 A1 | 8/2002 | Mizrahi |
| 2002/0193649 A1 | 12/2002 | O'Rear et al. |
| 2002/0198416 A1* | 12/2002 | Zhou et al. ............ 568/910 |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1* | 9/2003 | Zhou et al. ............ 568/488 |
| 2004/0006246 A1 | 1/2004 | Sherman et al. |
| 2004/0055955 A1 | 3/2004 | Davis |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0171779 A1 | 9/2004 | Matyjaszewski et al. |
| 2004/0187684 A1 | 9/2004 | Elomari |
| 2004/0188271 A1 | 9/2004 | Ramachandraiah et al. |
| 2004/0188324 A1 | 9/2004 | Elomari |
| 2004/0220433 A1 | 11/2004 | Van Der Heide |
| 2005/0027084 A1 | 2/2005 | Clarke |
| 2005/0038310 A1 | 2/2005 | Lorkovic et al. |
| 2005/0042159 A1 | 2/2005 | Elomari |
| 2005/0047927 A1 | 3/2005 | Lee et al. |
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0218041 A1 | 10/2005 | Yoshida et al. |
| 2005/0234276 A1 | 10/2005 | Waycuilis |
| 2005/0234277 A1 | 10/2005 | Waycuilis |
| 2005/0245771 A1 | 11/2005 | Fong et al. |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon et al. |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |
| 2007/0078285 A1 | 4/2007 | Dagle |
| 2007/0100189 A1 | 5/2007 | Stauffer |
| 2007/0129584 A1 | 6/2007 | Basset |
| 2007/0142680 A1 | 6/2007 | Ayoub |
| 2007/0148067 A1 | 6/2007 | Zones |
| 2007/0148086 A1 | 6/2007 | Zones |
| 2007/0149778 A1 | 6/2007 | Zones |
| 2007/0149789 A1 | 6/2007 | Zones |
| 2007/0149819 A1 | 6/2007 | Zones |
| 2007/0149824 A1 | 6/2007 | Zones |
| 2007/0149837 A1 | 6/2007 | Zones |
| 2007/0149838 A1 | 6/2007 | Chretien |
| 2007/0197801 A1 | 8/2007 | Bolk |
| 2007/0197847 A1 | 8/2007 | Liu |
| 2007/0213545 A1 | 9/2007 | Bolk |
| 2007/0238905 A1 | 10/2007 | Arredondo |
| 2007/0238909 A1* | 10/2007 | Gadewar et al. ............ 585/16 |
| 2007/0276168 A1 | 11/2007 | Garel |
| 2007/0284284 A1 | 12/2007 | Zones |
| 2008/0022717 A1 | 1/2008 | Yoshida et al. |
| 2008/0152555 A1 | 6/2008 | Wang et al. |
| 2008/0171898 A1 | 7/2008 | Waycuilis |
| 2008/0183022 A1 | 7/2008 | Waycuilis |
| 2008/0188697 A1 | 8/2008 | Lorkovic |
| 2008/0200740 A1 | 8/2008 | Waycuilis |
| 2008/0210596 A1 | 9/2008 | Litt et al. |
| 2008/0275279 A1 | 11/2008 | Podkolzin et al. |
| 2008/0275284 A1 | 11/2008 | Waycuilis |
| 2008/0314758 A1 | 12/2008 | Grosso et al. |
| 2009/0005620 A1 | 1/2009 | Waycuilis et al. |
| 2009/0163749 A1 | 6/2009 | Li et al. |
| 2009/0247796 A1 | 10/2009 | Waycuilis et al. |
| 2009/0270655 A1 | 10/2009 | Fong et al. |
| 2009/0306443 A1 | 12/2009 | Stark et al. |
| 2009/0308759 A1 | 12/2009 | Waycuilis |
| 2009/0312586 A1 | 12/2009 | Waycuilis et al. |
| 2009/0326292 A1 | 12/2009 | Waycuilis |
| 2010/0030005 A1 | 2/2010 | Sauer et al. |
| 2010/0087686 A1 | 4/2010 | Fong et al. |
| 2010/0096588 A1 | 4/2010 | Gadewar et al. |
| 2010/0099929 A1* | 4/2010 | Gadewar et al. ............ 570/101 |
| 2010/0099930 A1* | 4/2010 | Stoimenov et al. ............ 570/101 |
| 2010/0105972 A1 | 4/2010 | Lorkovic |
| 2010/0234637 A1 | 9/2010 | Fong et al. |
| 2010/0270167 A1* | 10/2010 | McFarland ............ 205/462 |
| 2011/0015458 A1 | 1/2011 | Waycuilis et al. |
| 2011/0071326 A1 | 3/2011 | Waycuilis |
| 2011/0130597 A1 | 6/2011 | Miller et al. |
| 2011/0198285 A1 | 8/2011 | Wallace |
| 2011/0218372 A1 | 9/2011 | Waycuilis et al. |
| 2011/0218374 A1 | 9/2011 | Waycuilis |
| 2012/0053381 A1 | 3/2012 | Evans et al. |
| 2012/0141356 A1 | 6/2012 | Brickey et al. |
| 2012/0245399 A1 | 9/2012 | Kurukchi et al. |
| 2012/0313034 A1 | 12/2012 | Kurukchi et al. |
| 2013/0006024 A1 | 1/2013 | Kurukchi et al. |
| 2013/0046121 A1 | 2/2013 | Kurukchi et al. |
| 2013/0079564 A1 | 3/2013 | Waycuilis |
| 2013/0090504 A1 | 4/2013 | Roscoe et al. |
| 2013/0102820 A1 | 4/2013 | Waycuilis et al. |
| 2013/0102821 A1 | 4/2013 | Waycuilis et al. |
| 2013/0156681 A1 | 6/2013 | Kurukchi et al. |
| 2013/0158324 A1 | 6/2013 | Waycuilis et al. |
| 2013/0178675 A1 | 7/2013 | Kurukchi et al. |
| 2013/0217938 A1 | 8/2013 | Waycuilis et al. |

FOREIGN PATENT DOCUMENTS

| | | |
|---|---|---|
| CA | 1202610 | 4/1986 |
| CA | 2542857 | 5/2005 |
| CA | 2236126 | 8/2006 |
| CA | 2203115 | 9/2006 |
| CA | 2510093 | 12/2006 |
| CA | 2641348 A1 | 8/2007 |
| CA | 2684765 A1 | 11/2008 |
| CN | 102099316 | 6/2011 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |

(56) References Cited

FOREIGN PATENT DOCUMENTS

| | | |
|---|---|---|
| EP | 0346612 B1 | 8/1993 |
| EP | 0560546 A1 | 9/1993 |
| EP | 0976705 A1 | 2/2000 |
| EP | 1186591 A2 | 3/2002 |
| EP | 1253126 A1 | 10/2002 |
| EP | 1312411 A2 | 5/2003 |
| EP | 1235769 B1 | 5/2004 |
| EP | 1435349 A2 | 7/2004 |
| EP | 1440939 A1 | 7/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 0/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 A | 11/1961 |
| GB | 930341 A | 7/1963 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 2185754 A | 7/1987 |
| GB | 2191214 A | 12/1987 |
| SU | 694483 A1 | 10/1979 |
| WO | 83/00859 | 3/1983 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/06039 A1 | 4/1993 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A1 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006/067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/083427 A2 | 8/2006 |
| WO | 2006/100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 A1 | 3/2008 |
| WO | 2008/036563 A2 | 3/2008 |
| WO | 2008/106318 A1 | 9/2008 |
| WO | 2008/106319 A1 | 9/2008 |
| WO | 2008/157043 A1 | 12/2008 |
| WO | 2008/157044 A1 | 12/2008 |
| WO | 2008/157045 A1 | 12/2008 |
| WO | 2008/157046 A1 | 12/2008 |
| WO | 2008/157047 A1 | 12/2008 |
| WO | 2009/152403 A1 | 12/2009 |

(56) References Cited

FOREIGN PATENT DOCUMENTS

| WO | 2009/152405 A1 | 12/2009 |
| WO | 2009/152408 A1 | 12/2009 |
| WO | 2010/009376 A1 | 1/2010 |
| WO | 2011/008573 A1 | 1/2011 |

OTHER PUBLICATIONS

U.S. Office Communication from U.S. Appl. No. 10/826,885 dated Oct. 31, 2005.
U.S. Office Communication from U.S. Appl. No. 10/826,885 dated Apr. 19, 2006.
U.S. Office Communication from U.S. Appl. No. 10/826,885 dated Jul. 27, 2006.
U.S. Office Communication from U.S. Appl. No. 10/826,885 dated Nov. 2, 2006.
U.S. Office Communication from U.S. Appl. No. 10/826,885 dated Jan. 24, 2007.
U.S. Office Communication from U.S. Appl. No. 10/893,418 dated Jun. 14, 2007.
U.S. Office Communication from U.S. Appl. No. 10/893,418 dated Jan. 2, 2008.
U.S. Office Communication from U.S. Appl. No. 11/091,130 dated Oct. 3, 2007.
U.S. Office Communication from U.S. Appl. No. 11/101,886 dated Jan. 24, 2007.
U.S. Office Communication from U.S. Appl. No. 11/254,438 dated Jan. 24, 2007.
U.S. Office Communication from U.S. Appl. No. 11/254,438 dated Nov. 1, 2007.
U.S. Office Communication from U.S. Appl. No. 11/778,479 dated Feb. 22, 2010.
U.S. Office Communication from U.S. Appl. No. 12/112,926 dated Jan. 16, 2009.
U.S. Office Communication from U.S. Appl. No. 12/112,926 dated Sep. 14, 2009.
U.S. Office Communication from U.S. Appl. No. 12/112,926 dated Jan. 7, 2010.
U.S. Office Communication from U.S. Appl. No. 12/112,926 dated Jul. 22, 2010.
U.S. Office Communication from U.S. Appl. No. 12/112,926 dated Jan. 7, 2011.
U.S. Office Communication from U.S. Appl. No. 12/123,924 dated Mar. 19, 2010.
U.S. Office Communication from U.S. Appl. No. 12/123,924 dated Aug. 30, 2010.
U.S. Office Communication from U.S. Appl. No. 12/139,135 dated Nov. 24, 2010.
U.S. Office Communication from U.S. Appl. No. 12/139,135 dated Apr. 14, 2011.
U.S. Office Communication from U.S. Appl. No. 12/139,135 dated Oct. 14, 2011.
U.S. Office Communication from U.S. Appl. No. 12/139,135 dated Nov. 7, 2013.
U.S. Office Communication from U.S. Appl. No. 12/477,307 dated Oct. 7, 2011.
U.S. Office Communication from U.S. Appl. No. 12/477,307 dated Feb. 27, 2012.
U.S. Office Communication from U.S. Appl. No. 12/477,319 dated Jul. 22, 2011.
U.S. Office Communication from U.S. Appl. No. 12/502,024 dated Oct. 26, 2010.
U.S. Office Communication from U.S. Appl. No. 12/502,024 dated May 31, 2011.
U.S. Office Communication from U.S. Appl. No. 12/502,024 dated Sep. 16, 2011.
U.S. Office Communication from U.S. Appl. No. 12/715,526 dated Feb. 17, 2011.
U.S. Office Communication from U.S. Appl. No. 12/715,526 dated May 24, 2011.
U.S. Office Communication from U.S. Appl. No. 12/715,526 dated Jan. 4, 2012.
U.S. Office Communication from U.S. Appl. No. 12/792,335 dated Aug. 17, 2012.
U.S. Office Communication from U.S. Appl. No. 12/792,335 dated Jan. 2, 2013.
U.S. Office Communication from U.S. Appl. No. 12/957,036 dated Aug. 16, 2012.
U.S. Office Communication from U.S. Appl. No. 13/053,540 dated Aug. 6, 2013.
U.S. Office Communication from U.S. Appl. No. 13/053,540 dated Jan. 8, 2014.
U.S. Office Communication from U.S. Appl. No. 13/117,785 dated Mar. 14, 2013.
U.S. Office Communication from U.S. Appl. No. 13/117,785 dated Apr. 22, 2013.
U.S. Office Communication from U.S. Appl. No. 13/157,584 dated May 11, 2012.
U.S. Office Communication from U.S. Appl. No. 13/157,584 dated Aug. 29, 2012.
U.S. Office Communication from U.S. Appl. No. 13/173,847 dated Sep. 6, 2013.
U.S. Office Communication from U.S. Appl. No. 13/173,847 dated Jan. 21, 2014.
U.S. Office Communication from U.S. Appl. No. 13/212,291 dated May 10, 2013.
U.S. Office Communication from U.S. Appl. No. 13/269,683 dated Jun. 6, 2013.
U.S. Office Communication from U.S. Appl. No. 13/647,002 dated Jun. 5, 2013.
U.S. Office Communication from U.S. Appl. No. 13/679,600 dated Jan. 17, 2014.
U.S. Office Communication from U.S. Appl. No. 13/713,926 dated Jan. 30, 2014.
U.S. Office Communication from U.S. Appl. No. 13/760,291 dated Apr. 4, 2014.
U.S. Appl. No. 60/487,364, filed Jul. 15, 2003, Lorkovic et al.
U.S. Appl. No. 60/559,844, filed Apr. 6, 2004, Sherman et al.
U.S. Appl. No. 60/765,115, filed Feb. 3, 2006, Gadewar et al.
Henshuiinkai, Kagaku Daijiten; Kagaku Daijiten 4, Japan, Kyoritsu Publisher, Oct. 15, 1963; pp. 652-654.
Jackisch, Philip F.; "Bromine" in Kirk-Othmer Encyclopedia of Chemical Technology, 4th Edition, vol. 4; pp. 536-537, 548-550, 560; Published 1992, John Wiley & Sons, Inc. USA.
Jacobson, C.A.; "Encyclopedia of Chemical Reactions"; vol. 1, 1946; p. 722.
Kesner, Miri; "How is Bromine Produced" in Bromine Compounds from the Dead Sea, Israel Products in the Service of People; pp. 3, 5, 78, 87; First published in Hebrew in Israel in 1999 by the Department of Science Teaching; The Weizmann Institute of Science.
Lewis, Sr., Richard J.; "Hawley's Condensed Chemical Dictionary", 15th Edition; Jan. 2007; John Wiley & Sons; p. 181.
Mills, Jack F.; "Bromine" in Ullmann's Encyclopedia of Industrial Chemistry, Fifth, Completely Revised Edition, vol. A4; pp. 391 and 397; Published 1985; VCH Verlagsgesellschaft mbH, Federal Republic of Germany.
Abstract of BE 812868, Aromatic hydrocarbons prodn. from chlorinated hydrocarbons, Publication date: Sep. 27, 1974, esp@cenet database—worldwide.
Abstract of BE 814900, Volatile aramatic cpds. prodn., Publication date: Sep. 2, 1974, esp@cenet database—worldwide.
Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.
Abstract of CA 2447761 A1, Oxidative halogenation of C1 hydrocarbons to halogenated C1 hydrocarbons and integrated processes related thereto, Publication date: Nov. 28, 2002, Inventor: Hickman, et al.
Abstract of CA 2471295 A1, Integrated process for synthesizing alcohols, ethers, and olefins from alkanes, Publication date: Jul. 31, 2003, Inventor: Sherman et al.

(56) References Cited

OTHER PUBLICATIONS

Abstract of CN 1199039, Pentanol and its production process, Publication date: Nov. 18, 1998, Inventor: Kailun, esp@cenet database—worldwide.
Abstract of CN 1210847, Process for producing low carbon alcohol by directly hydrating low carbon olefines, Publication date: Mar. 17, 1999, Inventor: Zhenguo et al., esp@cenet database—worldwide.
Abstract of CN 1321728, Method for preparing aromatic hydrocarbon and hydrogen gas by using law-pressure gas, Publication date: Nov. 14, 2001, Inventor: Jie et al., esp@cenet database—worldwide.
Abstract of CN 1451721, Process for non-catalytic combustion deoxidizing coal mine gas for producing methanol, Publication date: Oct. 29, 2003, Inventor: Pengwan et al., esp@cenet database—worldwide.
Abstract of CN 1623969, Method for preparing 1, 4-benzene dimethanol, Publication date: Jun. 8, 2005, Inventor: Jiarong et al., esp@cenet database—worldwide.
Abstract of CN 1657592, Method for converting oil to multiple energy fuel product, Publication date: Aug. 24, 2005, Inventor: Li, esp@cenet database—worldwide.
Abstract of CN 1687316, Method for producing biologic diesel oil from rosin, Publication date: Oct. 26, 2005, Inventor: Jianchun et al., esp@cenet database—worldwide.
Abstract of CN 1696248, Method for synthesizing biologic diesel oil based on ion liquid, Publication date: Nov. 16, 2005, Inventor: Sun, esp@cenet database—worldwide.
Abstract of CN 1699516, Process for preparing bio-diesel-oil by using miroalgae fat, Publication date: Nov. 23, 2005, Inventor: Miao, esp@cenet database—worldwide.
Abstract of CN 1704392, Process for producing alkylbenzene, Publication date: Dec. 7, 2005, Inventor: Gao, esp@cenet database—worldwide.
Abstract of CN 1724612, Biological diesel oil catalyst and method of synthesizing biological diesel using sai catalyst, Publication date: Jan. 25, 2006, Inventor: Gu, esp@cenet database—worldwide.
Abstract of CN 1986737, Process for producing biodiesel oil with catering waste oil, Publication date: Jun. 27, 2007, Inventor: Chen, esp@cenet database—worldwide.
Abstract of CN 100999680, Esterification reaction tech. of preparing biodiesel by waste oil, Publication date: Jul. 18, 2007, Inventor: Weiming, esp@cenet database—worldwide.
Abstract of CN 101016229, Refining method for bromomeoamyl alcohol, Publication date: Aug. 15, 2007, Inventor: Tian, esp@cenet database—worldwide.
Abstract of DE 3209964, Process for the preparation of chlorinated hydrocarbons, Publication date: Nov. 11, 1982, Inventor: Pyke et al., esp@cenet database—worldwide.
Abstract of DE 3210196, Process for the preparation of a monochlorinated olefin, Publication date: Jan. 5, 1983, Inventor: Pyke et al., esp@cenet database—worldwide.
Abstract of DE 3226028, Process for the preparation of monochlorinated olefin, Publication date: Feb. 3, 1983, Inventor: Pyke et al., esp@cenet database—worldwide.
Abstract of DE 3334225, Process for the preparation of 1,2-dichloroethane, Publication date: Apr. 4, 1985, Inventor: Hebgen et al., esp@cenet database—worldwide.
Abstract of DE 4232056, 2,5-Di:methyl-hexane-2,5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE 4434823, Continuous prodn. of hydroxy-benzyl alkyl ether, Publication date: Apr. 4, 1996, Inventor: Stein et al., esp@cenet database—worldwide.
Abstract of EP 0021497 (A1),Synthesis of polyoxyalkylene glycol monoalkyl ethers., Publication date: Jan. 7, 1981, Inventor: Gibson, esp@cenet database—worldwide.
Abstract of EP 0039471, Process for the preparation of 2-chloro-1,1,1,2,3,3,3-heptafluoropropane., Publication date: Nov. 11, 1981, Inventor: Von Halasz, esp@cenet database—worldwide.

Abstract of EP 0101337, Process for the production of methylene chloride., Publication date: Feb. 22, 1984, Inventor: Olah et al., esp@cenet database—worldwide.
Abstract of EP 0235110, Process for the stabilization of silicalite catalysts., Publication date: Sep. 2, 1987, Inventor: Debras et al., esp@cenet database—worldwide.
Abstract of EP 0407989, Method for the production of 1,1,1-trifluoro-2,2-dichloroethane by photochlorination., Publication date: Jan. 16, 1991, Inventor: Cremer et al., esp@cenet database—worldwide.
Abstract of EP 0442258, Process for the preparation of a polyunsaturated olefin., Publication date: Aug. 21, 1991, Inventor: Gaudin et al., esp@cenet database, worldwide.
Abstract of EP 0465294, Process for the preparation of unsaturated bromides., Publication date: Jan. 8, 1992, Inventor: Decaudin et al., esp@cenet database—worldwide.
Abstract of EP 0549387, Synthesis of n-perfluorooctylbromide., Publication date: Jun. 30, 1993, Inventor: Drivon et al., esp@cenet database—worldwide.
Abstract of EP 0850906, Process and apparatus for the etherification of olefinic hydrocarbon feedstocks, Publication date: Jul. 1, 1998, Inventor: Masson, esp@cenet database—worldwide.
Abstract of EP 0858987, Process for conversion of lighter alkanes to higher hydrocarbons, Publication date: Aug. 19, 1998, Inventor: Amariglio, et al., esp@cenet database—worldwide.
Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.
Abstract of EP 1404636, Integrated process for synthesizing alcohols and ethers from alkanes, Publication date: Apr. 7, 2004, Inventor: Zhou et al., esp@cenet database—worldwide.
Abstract of EP 1435349 A2, Integrated process for synthesizing alcohols and ethers from alkanes, Publication date: Jul. 7, 2004, Inventor: Zhou et al.
Abstract of EP 1474371, Integrated process for synthesizing alcohols, ethers, and olefins from alkanes, Publication date: Nov. 10, 2004, Inventor: Zhou et al., esp@cenet database—worldwide.
Abstract of FR 2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR 2880019, Manufacturing 1,2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR 2883870, Formation of 1,2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR 2883871, Preparing 1,2-dichloroethane comprises cracking hydrocarbon to form mixture, sending mixture into storage reservoir, supplying mixture into chlorination and/or oxychloration reactor, and separating 1,2-dichloroethane from reactor, Publication date: Oct. 6, 2006, Inventor: Balthasart et al., esp@cenet database—worldwide.
Abstract of IT 1255246, Process for the preparation of dinitrodiphenylmethanes, Publication date: Oct. 20, 1995, Applicant: Enichem Spa et al., esp@cenet database—worldwide.
Abstract of IT 1255358, Process for the synthesis of 1,4-butanediol, Publication date: Oct. 31, 1995, Inventor: Ricci Marco, esp@cenet database—worldwide.
Abstract of JP 2142740, Production of fluoroalcohol, Publication date: May 31, 1990, Inventor: Tsutomu et al., esp@cenet database—worldwide.
Abstract of JP 2144150, Chemical process and catalyst used therefore, Publication date: Jun. 1, 1990, Inventor: Deidamusu et al., esp@cenet database—worldwide.

(56) References Cited

OTHER PUBLICATIONS

Abstract of JP 4305542, Production of halogenated hydrocarbon compounds, Publication date: Oct. 28, 1992, Inventor: Shinsuke et al., esp@cenet database—worldwide.
Abstract of JP 6172225, Method for fluorinating halogenated hydrocarbon, Publication date: Jun. 21, 1994, Inventor: Takashi et al., esp@cenet database—worldwide.
Abstract of JP 6206834, Production of Tetrachloroethanes, Publication date: Jul. 26, 1994, Inventor: Toshiro et al., esp@cenet database—worldwide.
Abstract of JP 8266888, Method for decomposing aromatic halogen compound, Publication date: Oct. 15, 1996, Inventor: Yuuji et al., esp@cenet database—worldwide.
Abstract of JP 2001031605, Production of 3-hydroxy-1-cycloalkene, Publication date: Feb. 6, 2001, Inventor: Hideo et al., esp@cenet database—worldwide.
Abstract of JP 2004-529189.
Abstract of JP 2004075683, Method for producing optically active halogenohydroxypropyl compound and glycidyl compound, Publication date: Mar. 11, 2004, Inventor: Keisuke et al., esp@cenet database—worldwide.
Abstract of JP 2004189655, Method for fluorinating with microwave, Publication date: Jul. 8, 2004, Inventor: Masaharu et al., esp@cenet database—worldwide.
Abstract of JP 2005075798, Method for producing adamantyl ester compound, Publication date: Mar. 24, 2005, Inventor: Norihiro et al., esp@cenet database—worldwide.
Abstract of JP 2005082563, Method for producing 1,3-adamantanediol, Publication date: Mar. 31, 2005, Inventor: Norihiro et al., esp@cenet database—worldwide.
Abstract of JP 2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP 2005254092, Method of manufacturing alkynes, Publication date: Sep. 22, 2005, Inventor: Shirakawa Eiji, esp@cenet database—worldwide.
Abstract of JP 2006151892, Preparation method of alcohol derivative, Publication date: Jun. 15, 2006, Inventor: Baba Akio et al., esp@cenet database—worldwide.
Abstract of JP 2006152263, Organic-inorganic hybrid-type mesoporous material, method for producing the same, and solid catalyst, Publication date: Jun. 15, 2006, Inventor: Junko et al., esp@cenet database—worldwide.
Abstract of JP 2006193473, Aryl polyadamantane derivative having carboxy or acid anhydride group and method for producing the same, Publication date: Jul. 27, 2006, Inventor: Yasuto et al, esp@cenet database—worldwide.
Abstract of JP 2006231318, Phosphorus containing macromolecule immobilizing palladium catalyst and method for using the same, Publication date: Sep. 7, 2006, Inventor: Osamu et al., esp@cenet database—worldwide.
Abstract of JP 2006263567, Optical resolution method of optical isomer and optical resolution device, Publication date: Oct. 5, 2006, Inventor: Yoshikazu et al., esp@cenet database—worldwide.
Abstract of JP 2006265157, Method for catalytically activating silicated nucleating agent using phosphazene base, Publication date: Oct. 5, 2006, Inventor: Yoshinori et al., esp@cenet database—worldwide.
Abstract of JP 2006306758, Method for producing biaryl compound, Publication date: Nov. 9, 2006, Inventor: Yuji et al., esp@cenet database—worldwide.
Abstract of JP 2007001942, Production method of para-xylene, Publication date: Jan. 11, 2007, Inventor: Kazuyoshi, esp@cenet database—worldwide.
Abstract of JP 2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.
Abstract of JP 2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP 2007061594, Method for decomposing organohalogen compound and mobile decomposition system, Publication date: Mar. 15, 2007, Inventor: Koichi et al., esp@cenet database—worldwide.
Abstract of JP 2007099729, Method for producing alpha-methylstyrene or cumene, Publication date: Apr. 19, 2007, Inventor: Toshio, esp@cenet database—worldwide.
Abstract of RO 119778, Process for preparing perchloroethylene, Publication date: Mar. 30, 2005, Inventor: Horia et al., esp@cenet database—worldwide.
Abstract of WO 0105737, Method for preparing a carboxylic acid, Publication date: Jan. 25, 2001, Inventor: Pascal et al., esp@cenet database—worldwide.
Abstract of WO 0105738, Method for Preparing a carboxylic acid, Publication date: Jan. 25, 2001, Inventor: Pascal et al., esp@cenet database—worldwide.
Abstract of WO 9721656, Method for making fluoroalkanols, Publication date: Jun. 19, 1997, Inventor: Gillet, esp@cenet database—worldwide.
Abstract of WO 9950213, Method for producing dialkyl ethers, Publication date: Oct. 7, 1999, Inventor: Falkowski et al., esp@cenet database—worldwide.
Abstract of WO 2004092099, Method for producing cyclic enols, Publication date: Oct. 28, 2004, Inventor: Friedrich Marko et al., esp@cenet database—worldwide.
Abstract of WO 2006063852, Electroluminescent polymers and use thereof, Publication date: Jun. 22, 2006, Inventor: Buesing Arne et al., esp@cenet database—worldwide.
Abstract of WO 2006076942, Method for the production of synthetic fuels from oxygenates, Publication date: Jul. 27, 2006, Inventor: Rothaemel et al., esp@cenet database—worldwide.
Abstract of WO 2006136135, Method for decarboxylating C-C cross-linking of carboxylic acids with carbon electrophiles, Publication date: Dec. 28, 2006, Inventor: Goossen Lukas et al., esp@cenet database—worldwide.
Abstract of WO 2007028761, Method for chlorinating alcohols, Publication date: Mar. 15, 2007, Inventor: Rohde et al., esp@cenet database—worldwide.
Abstract of WO 2007128842, Catalytic transalkylation of dialkyl benzenes, Publication date: Nov. 15, 2007, Inventor: Goncalvesalmeida et al., esp@cenet database—worldwide.
Abstract of WO 2007137566, Method for catalytic conversion of organic oxygenated compounds from biomaterials, Publication date: Dec. 6, 2007, Inventor: Reschetilowski, esp@cenet database—worldwide.
Adachi et al., Synthesis of sialyl lewis X ganglioside analogs containing a variable length spacer between the sugar and lipophilic moieties, J. Carbohydrate Chemistry, vol. 17, No. 4-5, 1998, pp. 595-607, XP009081720.
Akhrem et al., Ionic Bromination of Ethane and other alkanes (cycloalkanes) with bromine catalyzed by the polyhalomethane-2AlBr3 aprotic organic superacids under mild conditions, Tetrahedron Letters, vol. 36, No. 51, 1995, pp. 9365-9368, Pergamon, Great Britain.
Bagno et al., Superacid-catalyzed carbonylation of methane, methyl halides, methyl alcohol, and dimethyl ether to methyl acetate and acetic acid, J. Org. Chem. 1990, 55, pp. 4284-4289, Loker Hydrocarbon Research Institute; University of Southern California.
Bakker et al., An exploratory study of the addition reactions of ethyleneglycol, 2-chloroethanol and 1,3-dichloro-2-propanol to 1-dodecene, J. Am. Oil Chem. Soc., vol. 44, No. 9, 1967, pp. 517-521, XP009081570.
Benizri et al., Study of the liquid-vapor equilibrium in the bromine-hydrobromic acid-water system, Hydrogen Energy Vector, 1980, pp. 101-116.
Bouzide et al., Highly selective silver (I) oxide mediated monoprotection of symmetrical diols, Tetrahedron Letters, Elsevier, vol. 38, No. 34, 1997, pp. 5945-5948, XP004094157.

(56) References Cited

OTHER PUBLICATIONS

Bradshaw et al., Production of hydrobromic acid from bromine and methane for hydrogen production, Proceedings of the 2001 Doe Hydrogen Program Review, NREL/CP-570-30535, 2001, pp. 1-8.
Chang et al., The conversion of methanol and other O-compounds to hydrocarbons over zeolite catalysts, Journal of Catalysis 47, 1977, Academic Press, Inc., pp. 249-259.
Claude et al., Monomethyl-branching of long n-alkanes in the range from decane to tetracosane on Pt/H-ZSM-22 bifunctional catalyst, Journal of Catalysis 190, 2000, pp. 39-48.
Combined International Search Report and Written Opinion dated Apr. 17, 2007 for PCT/US2006/013394, Applicant: GRT, Inc. , pp. 1-13.
Driscoll, Direct methane conversion, Federal Energy Technology Center, U.S. Department of Energy, M970779, pp. 1-10.
Fenelonov, et al., Changes in texture and catalytic activity of nanocrystalline MgO during its transformation to MgCl2 in the reaction with 1-chlorobutane, J. Phys. Chem. B 2001, 105, 2001 American Chemical Society, pp. 3937-3941.
Final Report, Abstract, http://chemelab.ucsd.edu/methanol/memos/final.html, May 9, 2004, pp. 1-7.
Gibson, Phase-transfer synthesis of monoalkyl ethers of oligoethylene glycols, J. Org. Chem. 1980, vol. 45, No. 6, pp. 1095-1098, XP002427776.
http://webbook.nist.gov/, Welcome to the NIST chemistry webbook, Sep. 10, 2007, U.S. Secretary of Commerce on Behalf of the United States of America, pp. 1-2.
Ione, et al., Syntheses of hydrocarbons from compounds containing one carbon atom using bifunctional zeolite catalysts, Solid Fuel Chemistry, Khimiya Tverdogo Topliva, 1982, Allerton Press, Inc., vol. 16, No. 6, pp. 29-43.
Jaumain et al., Direct catalytic conversion of chloromethane to higher hydrocarbons over various protonic and cationic zeolite catalysts as studied by in-situ FTIR and catalytic testing, Studies in Surface Science and Catalysis 130, Elsevier Science B.V., 2000, pp. 1607-1612.
JLM Technology Ltd., The Miller GLS Technology for conversation of light hydrocarbons to alcohols, New Science for the Benefit of Humanity, May 31, 2000; pp. 1-10.
Kirk-Othmer, Encyclopedia of Chemical Technology, 4th Edition, vol. 1, A Wiley-Interscience Publication, John Wiley & Sons, 1991, pp. 946-997.
Liu et al., Higher hydrocarbons from methane condensation mediated by HBr, Journal of Molecular Catalysis A: Chemical 273, Elsevier B.V., 2007, pp. 14-20.
Loiseau et al., Multigram synthesis of well-defined extended bifunctional polyethylene glycol (PEG) chains, J. Org. Chem., vol. 69, No. 3, XO-002345040, 2004, pp. 639-647.
Lorkovic et al., A novel integrated process for the functionalization of methane and ethane: bromine as mediator, Catalysis Today 98, 2004, pp. 317-322.
Lorkovic et al., C1 oxidative coupling via bromine activation and tandem catalytic condensation and neutralization over CaO/zeolite composites II. Product distribution variation and full bromine confinement, Catalysis Today 98, 2004, pp. 589-594.
Lorkovic et al., C1 coupling via bromine activation and tandem catalytic condensation and neutralization over CaO/zeolite composites, Chem. Comm. 2004, pp. 566-567.
Mihai, et al., Application of Bronsted-type LFER in the study of the phospholipase C Mechanism, J. Am. Chem. Soc., vol. 125, No. 11, XP-002427777, 2003, pp. 3236-3242.
Mishakov et al., Nanocrystalline MgO as a dehydrohalogenation catalyst, Journal of Catalysis 206, Elsevier Science, USA, 2002, pp. 40-48.
Mochida, et al., The catalytic dehydrohalogenation of haloethanes on solid acids and bases, Bulletin of the Chemical Society of Japan, vol. 44, Dec. 1971, pp. 3305-3310.
Motupally et al., Recycling chlorine from hydrogen chloride, The Electrochemical Society Interface, Fall 1998, pp. 32-36.

Murray et al., Conversion of methyl halides to hydrocarbons on basic zeolites: a discovery by in situ NMR, J. Am. Chem. Soc., 1993, vol. 115, pp. 4732-4741.
Nishikawa et al., Ultrasonic relaxations in aqueous solutions of alcohols and the balance between hydrophobicity and hydrophilicity of the solutes, J. Phys. Chem., vol. 97, No. 14, XP-002427775, 1993, pp. 3539-3544.
Olah et al., Antimony pentafluoride/graphite catalyzed oxidative carbonylation of methyl halides with carbon monoxide and copper oxides (or copper/oxygen) to methyl acetate, J. Org. Chem. 1990, 55, pp. 4293-4297.
Olah et al., Antimony pentafluoride/graphite catalyzed oxidative conversion of methyl halides with copper oxides (or copper/oxygen) to dimethyl ether, J. Org. Chem. 1990, 55, pp. 4289-4293.
Olah, Electrophilic methane conversion, American Chemical Society, Acc. Chem. Res. 1987, 20, pp. 422-428.
Olah, Hydrocarbons through methane derivatives, Hydrocarbon Chemistry, 1995, pp. 89-90, John Wiley & Sons, Inc.
Olah et al., Hydrocarbons through methane derivatives, Hydrocarbon Chemistry, 2nd Edition, 2003, pp. 123, 149, and 153, John Wiley & Sons, Inc.
Olah et al., Onium Ylide Chemistry. 1. Bifunctional acid-base-catalyzed conversion of heterosubstituted methanes into ethylene and derived hydrocarbons. The Onium Ylide mechanism of the C1-C2 conversion. J. Am. Chem. Soc. 1984, 106, pp. 2143-2149.
Olah et al., Selective monohalogenation of methane over supported acid or platinum metal catalysts and hydrolysis of methyl halides over y-alumina-supported metal oxide/hydroxide catalysts. A feasible path for the oxidative conversion of methane into methyl alcohol/dimethyl ether., J. Am. Chem. Soc. 1985, 107, pp. 7097-7105.
Prelog et al., 234. Chirale 2, 2'-polyoxaalkano-9,9'-spirobifluorene, Helvetica Chimica ACTA, vol. 62, No. 7, 1979 pp. 2285-2302.
Rakoff et al., Quimica Organica Fundamental, Organic Chemistry, The Macmillan Company, 1966, pp. 58-63 and 76-77.
Richards, et al., Nanocrystalline ultra high surface area magnesium oxide as a selective base catalyst, Scripta Materialia, 44, 2001, pp. 1663-1666, Elsevier Science Ltd.
Shimizu et al., Gas-Phase electrolysis of hydrobromic acid using PTFE-bonded carbon electrode, Int. J. Hydrogen Energy, vol. 13, No. 6, pp. 345-349, 1988.
Smirnov et al., Selective bromination of alkanes and arylalkanes with CBr4, Mendeleev Commun., 2000, pp. 175-176.
Sun et al., Nanocrystal metal oxide—Chlorine adducts: selective catalysts for chlorination of alkanes, J. Am. Chem. Soc., 1999, 121, pp. 5587-5588.
Sun et al., A general integrated process for synthesizing olefin oxides, Chem. Commun., The Royal Society of Chemistry 2004, pp. 2100-2101.
Tamura et al., The reactions of grignard reagents with transition metal halides: Coupling, disproportionation, and exchange with olefins, Bulletin of the Chemical Society of Japan, vol. 44, Nov. 1971, pp. 3063-3073.
Taylor et al., Direct conversion of methane to liquid hydrocarbons through chlorocarbon intermediates, 1988, Elsevier Science Publishers B.V. Amsterdam, Netherlands, pp. 483-489.
Taylor, Conversion of substituted methanes over ZSM-catalysts, 2000, pp. 3633-3638, Studies in Surface Science and Catalysis 130, Elsevier Science B.V.
Taylor, PETC's on-site naural gas conversion efforts, Preprints of the Fuel Division, 208th National Meeting of the American Chemical Society, 39 (4), 1994, pp. 1228-1232.
Thomas et al., Catalytically active centres in porous oxides: design and performance of highly selective new catalysts, Chem. Commun., 2001, pp. 675-687.
Thomas et al., Synthesis and characterization of a catalytically active nickel-silicoaluminophosphate catalyst for the conversion of methanol to ethene, American Chemical Society, 1991, 3, pp. 667-672.
Van Velzen et al., HBr electrolysis in the Ispra mark 13A flue gas desulphurization process: electrolysis in a DEM cell, Journal of Applied Electrochemistry, 20, 1990, pp. 60-68.
Wagner et al., Reactions of VX, GD, and HD with nanosize CaO: autocatalytic dehydrohalogenation of HD, J. Phys. Chem. B 2000, 104, pp. 5118-5123, 2000 American Chemical Society.

(56) References Cited

OTHER PUBLICATIONS

Wauters et al., Electrolytic membrane recovery of bromine from waste hydrogen bromide streams, AlChE Journal, Oct. 1998, vol. 44, No. 10, pp. 2144-2148.

Weissermel et al., Industrial Organic Chemistry, 3rd Edition, 1997, pp. 160-162, and 208.

Whitesides et al., Nuclear magnetic resonance spectroscopy. The effect of structure on magnetic nonequivalence due to molecular asymmetry, J. Am. Chem. Soc., vol. 86, No. 13, 1964, pp. 2628-2634, XP002427774.

Yilmaz et al., Bromine mediated partial oxidation of ethane over nanostructured zirconia supported metal oxide/bromide, Microporous and Mesoporous Materials, 79, 2005, Science Direct, Elsevier, pp. 205-214.

Zhou et al., An integrated process for partial oxidation of alkanes, Chem. Commun., 2003, The Royal Society of Chemistry, pp. 2294-2295.

ZSM-5 Catalyst, http://chemelba.ucsd.edu/methanol/memos/ZSM-5.html, Nov. 6, 2003, p. 1.

Abstract of GB 998681(A), Improvements in or relating to the recovery of bromine from bromine-containing materials, Publication date: Jul. 21, 1965, Applicant: Electro Chimie Metal+, espacenet worldwide database.

Abstract of JP 55-073619, Condensation of methyl chloride through dehydrochlorination, Publication date: Jun. 3, 1980, Inventor: Shigeo et al., http://www19.ipdl.inpit.go.jp/PA1/result . . . .

Hannus, Adsorption and transformation of halogenated hydrocarbons over zeolites, Applied Catalysis A: General 189, 1999, XP-002634422, pp. 263-276.

Howe, Zeolite catalysts for dehalogenation processes, Applied Catalysis A: General 271, 2004, XP-002634421, pp. 3-11.

Li et al., Pyrolysis of Halon 1301 over zeolite catalysts, Microporous and Mesoporous Materials 35-36, 2000, XP-002634423, pp. 219-226.

Chretien; Process for the Adjustment of the HHV in the LNG Plants; 23rd World Gas Conference; Amsterdam 2006; Jun. 5-9, 2006; pp. 1-14.

Yang et al.; Maximising the Value of Surplus Ethane and Cost-Effective Design to Handle Rich LNG; publ. date Jun. 1, 2007; pp. 1-13.

Abstract of JP Publication No. 08-283182; Production of Hydrochloromethanes; Published Oct. 29, 1996; Inventor: Miyazaki Kojiro et al., http://www19/ipdl.inpit.go.jp . . . .

Abstract of WO 96/00696; Method and Apparatus for Recovering Bromine from a Liquid Effluent; Published Jan. 11, 1996; Inventor: Mulet, Jean-Charles et al.

CN—Official Action for Chinese Application No. 201280061473.1 dated Mar. 2, 2015.

Extended European Search Report for EPC Application No. 12857349.0 dated Jul. 2, 2015.

* cited by examiner

PROCESSES AND SYSTEMS FOR CONVERSION OF ALKYL BROMIDES TO HIGHER MOLECULAR WEIGHT HYDROCARBONS IN CIRCULATING CATALYST REACTOR-REGENERATOR SYSTEMS

BACKGROUND OF THE INVENTION

The present invention relates generally to processes and systems for producing higher molecular weight hydrocarbons from lower molecular weight alkanes, and, in one or more embodiments, to processes and systems that include the conversion of alkyl bromides to higher molecular weight hydrocarbons in circulating catalyst reactor-regenerator systems.

Natural gas, a fossil fuel, is primarily composed of methane and other light alkanes and has been discovered in large quantities throughout the world. When compared to other fossil fuels, natural gas is generally a cleaner but lower-valued energy source. For example, crude oil typically contains impurities, such as heavy metals and high-molecular weight organic sulfides, which are generally not found in natural gas. By way of further example, burning natural gas, or hydrocarbon liquids derived from natural gas, produces far less carbon dioxide than burning coal. However, challenges are associated with the use of natural gas in place of other fossil fuels. Many locations in which natural gas has been discovered are far away from populated regions and, thus, do not have significant pipeline structure and/or market demand for natural gas. Due to the low density of natural gas, the transportation thereof in gaseous form to more populated regions can be expensive. Accordingly, practical and economic limitations exist to the distance over which natural gas may be transported in its gaseous form.

Cryogenic liquefaction of natural gas to form liquefied natural gas (often referred to as "LNG") is often used to more economically transport natural gas over large distances. However, this LNG process is generally expensive, and there are limited regasification facilities in only a few countries for handling the LNG. Converting natural gas to higher molecular weight hydrocarbons which, due to their higher density and value, are able to be more economically transported as a liquid can significantly expand the market for natural gas, particularly stranded natural gas produced far from populated regions. While a number of processes for the conversion of natural gas to higher molecular weight hydrocarbons have been developed, these processes have not gained widespread industry acceptance due to their limited commercial viability. Typically, these processes suffer from high capital and operating costs and/or relatively low carbon efficiencies that have limited their use.

BRIEF SUMMARY OF THE INVENTION

To achieve the foregoing and other objects, and in accordance with the purposes of the present invention, as embodied and broadly described herein, one embodiment of the present invention is a process comprising reacting at least alkyl bromides over a catalyst in at least one conversion reactor to produce at least an effluent stream comprising higher molecular weight hydrocarbons and hydrogen bromide. The process may further comprise removing a portion of the catalyst from the conversion reactor. The process may further comprise contacting the portion of the catalyst with a stripping gas to displace hydrocarbons from the portion of the catalyst. The process may further comprise contacting the portion of the catalyst with a first inert gas. The process may further comprise contacting the portion the catalyst with oxygen to form a regenerated catalyst by removal of coke. The process may further comprise contacting the regenerated catalyst with a second inert gas. The process may further comprise introducing at least a portion of the regenerated catalyst into the conversion reactor.

Another embodiment of the present invention is a process comprising reacting at least bromomethane over a crystalline alumino-silicate catalyst in at least one conversion reactor to produce at least an effluent stream comprising higher molecular weight hydrocarbons and hydrogen bromide. The process may further comprise introducing a portion of the catalyst from the conversion reactor into a two-stage stripping unit. The process may further comprise introducing a stripping gas into an upper stage of the two-stage stripping unit to displace hydrocarbons from the portion of the catalyst, the hydrocarbons comprising hydrocarbons having six or more carbon atoms. The process may further comprise introducing a first inert gas into a lower stage of the two-stage stripping unit to remove a quantity of the stripping gas from the portion of the catalyst. The process may further comprise introducing the portion of the catalyst from the two-stage stripping unit into a regeneration reactor to form a regenerated catalyst, wherein the portion of the catalyst is contacted with an oxygen-containing stream for coke removal. The process may further comprise introducing at least a portion of the regenerated catalyst into the conversion reactor.

Yet another embodiment of the present invention comprises a reactor system comprising a conversion reactor configured for reaction of at least alkyl bromides over a catalyst to produce at least a stream comprising higher molecular weight hydrocarbons and hydrogen bromide. The reactor system may comprise a two-stage stripping unit configured to receive a portion of the catalyst from the conversion reactor. The two-stage stripping unit may comprise a first stripping stage configured for contact of the portion of the catalyst with a stripping gas, and a second stripping stage configured for contact of the portion of the catalyst with an inert gas. The reactor system may further comprise a regeneration reactor configured for oxidation of the portion of the catalyst from the two-stage stripping unit, and a second stripping unit configured for contact of the portion of the catalyst from the regeneration reactor with an inert gas.

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings.

DETAILED DESCRIPTION OF THE PREFERRED EMBODIMENTS

Figure 1:
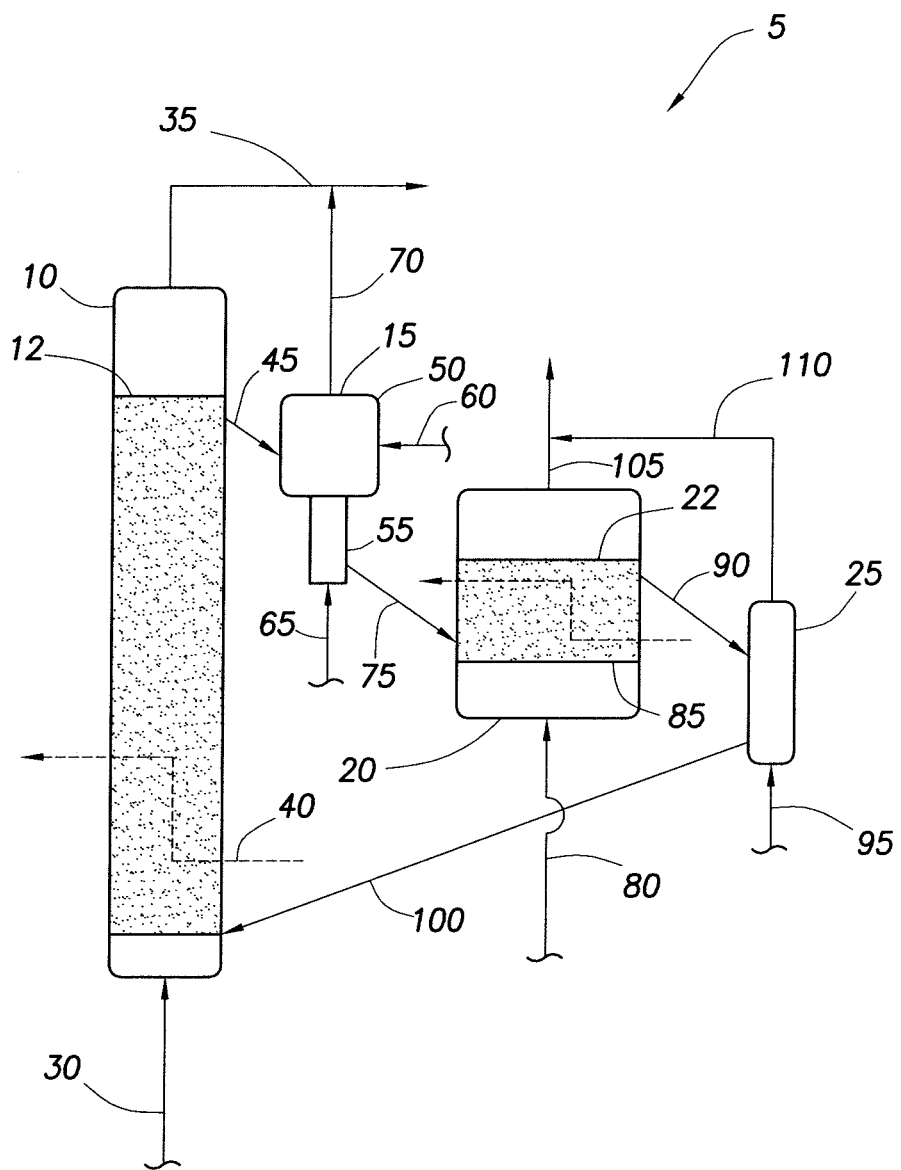
FIG. 1 is a schematic diagram of one embodiment of a reactor-regenerator system of the present invention.

Embodiments of the present invention disclose processes and systems that include the conversion of alkyl bromides to higher molecular weight hydrocarbons in circulating reactor-regenerator systems. In particular embodiments, the circulating reactor-regenerator systems utilize continuous or intermittent circulation of a solid catalyst between a conversion reactor and a regeneration process that includes a two-stage stripping unit.

There may be many potential advantages to the processes and systems of the present invention, only some of which are alluded to herein. One of the many potential advantages of embodiments of the processes and systems of the present invention is that use of the circulating catalyst reactor-regenerator systems in which the catalyst is continuously or intermittently regenerated should allow continuous reactor operation because regenerated catalyst is added to the conversion reactor as coke accumulates on the catalyst in the conversion reactor with deactivated catalyst withdrawn. Moreover, addition of the regenerated catalyst to the conversion reactor should minimize the amount of catalyst and reactor volume needed for a given amount of production. Even further, the two-stage stripping unit should allow for recovery of hydrocarbons from the catalyst prior to oxidative regeneration, thus minimizing carbon loss from the catalyst. In particular, at least a portion of the coke formed on the catalyst during alkyl bromide conversion may be in the form of C6+ hydrocarbons (e.g., aromatic compounds) which are produced, for example, within the crystalline cages of the catalyst, and which can be stripped from the catalyst and recovered prior to regeneration, in accordance with embodiments of the present invention.

The term "higher molecular weight hydrocarbons" as used herein refers to hydrocarbons comprising a greater number of carbon atoms than one or more components of the feedstock. For example, natural gas is typically a mixture of light hydrocarbons, predominately methane, with lesser amounts of ethane, propane, and butane, and even smaller amounts of longer chain hydrocarbons such as pentane, hexane, etc. When natural gas is used as a feedstock, higher molecular weight hydrocarbons produced in accordance with embodiments of the present invention may include a hydrocarbon comprising C2 and longer hydrocarbon chains, such as ethane, ethylene, propane, propylene, butane, butylenes, C5+ hydrocarbons, aromatic hydrocarbons, and mixtures thereof. In some embodiments, part or all of the higher molecular weight hydrocarbons may be used directly as a product (e.g., LPG, motor fuel, etc.). In other instances, part or all of the higher molecular weight hydrocarbons may be used as an intermediate product or as a feedstock for further processing. In yet other instances, part or all of the higher molecular weight hydrocarbons may be further processed, for example, to produce gasoline grade fuels, diesel grade fuels, and fuel components. In some embodiments, part or all of the higher molecular weight hydrocarbons obtained by the processes of the present invention can be used directly as a motor gasoline fuel having a substantial aromatic content, as a fuel blending stock, or as feedstock for further processing such as an aromatic feed to a process producing aromatic polymers such as polystyrene or related polymers.

The term "olefins," as used herein refers to hydrocarbons that contain two to six carbon atoms and at least one carbon-carbon double bond. In some embodiments, with some zeolite catalysts, olefins are produced in the reactor-regenerator systems discussed below along with other higher molecular weight hydrocarbons, such as ethane and propane, for example. The olefins may be further processed if desired. For instance, in some instances, the olefins produced by the processes of the present invention may be further reacted in a polymerization reaction (e.g., a reaction using a metallocene catalyst) to produce poly(olefins), which may be useful in many end products such as plastics or synthetic lubricants. In other embodiments, the olefins may be recycled back to the bromination stage, for example. It should be noted that the olefins (e.g., C2 and C3 olefins) are substantially more reactive than the respective alkane (ethane and propane) and are observed to be almost completely converted to di-bromoethylene and di-bromopropylene. Nevertheless, di-bromoethylene and di-bromopropylene can be efficiently converted to higher molecular weight hydrocarbons over zeolite catalysts.

The end use of the higher molecular weight hydrocarbons may depend on the particular catalyst employed for the coupling reaction carried out in the reactor-regenerator systems discussed below, as well as the operating parameters employed in the process. Other uses will be evident to those skilled in the art with the benefit of this disclosure.

The term "alkyl bromides," as used herein, refers to mono-, di-, and tri-brominated alkanes, and combinations of these. Poly-brominated alkanes include di-brominated alkanes, tri-brominated alkanes and mixtures thereof. These alkyl bromides may be reacted over suitable catalysts so as to form higher molecular weight hydrocarbons.

The term "lower molecular weight alkanes," as used herein, refers to methane, ethane, propane, butane, pentane or mixtures of two or more of these individual alkanes. Lower molecular weight alkanes may be used as a feedstock for the methods described herein. For example, the lower molecular weight alkanes may be reacted with bromine to produce alkyl bromides. The lower molecular weight alkanes may be from any suitable source, for example, any source of gas that provides lower molecular weight alkanes, whether naturally occurring or synthetically produced. Examples of sources of lower molecular weight alkanes for use in the processes of the present invention include, but are not limited to, natural gas, coal-bed methane, regasified liquefied natural gas, gas derived from gas hydrates and/or clathrates, gas derived from anaerobic decomposition of organic matter or biomass, gas derived in the processing of tar sands, and synthetically produced natural gas or alkanes. Combinations of these may be suitable as well in some embodiments. In some embodiments, it may be desirable to treat the feed gas to remove undesirable compounds, such as sulfur compounds and carbon dioxide.

Suitable sources of bromine that may be used in various embodiments of the present invention include, but are not limited to, elemental bromine, bromine salts, aqueous hydrobromic acid, metal bromide salts, and the like. Combinations may be suitable, but as recognized by those skilled in the art, using multiple sources may present additional complications.

Certain embodiments of the methods of the invention are described below. Although major aspects of what is to believed to be the primary chemical reactions involved in the methods are discussed in detail as it is believed that they occur, it should be understood that side reactions may take place. One should not assume that the failure to discuss any particular side reaction herein means that the side reaction does not occur. Conversely, those that are discussed should not be considered exhaustive or limiting. Additionally, although figures are provided that schematically show certain aspects of the methods of the present invention, these figures should not be viewed as limiting on any particular method of the invention.

FIG. 1 is a schematic diagram illustrating a reactor-regenerator system 5 in accordance with embodiments of the present invention. In the illustrated embodiment, the reactor-regenerator system 5 includes the following: a conversion reactor 10 for converting alkyl bromides to higher molecular weight hydrocarbons; a two-stage stripping unit 15 for receiving deactivated catalyst from the conversion reactor 10 and recovering hydrocarbons there from; a regeneration reactor 20 for receiving the stripped, deactivated catalyst from the two-stage stripping unit 15 and removing coke deposits there from by oxidative regeneration; and a second stripping unit 25 for receiving the regenerated catalyst from the regeneration reactor 20 and removing residual oxygen and other components there from. As previously mentioned, employment of the two-stage stripping unit 15 may allow for recovery of hydrocarbons from the catalyst prior to regeneration, which can minimize carbon loss while maximizing process efficiency, in accordance with embodiments of the present invention.

As illustrated, a feed stream 30 may be introduced to the conversion reactor 10. The feed stream 30 introduced to the conversion reactor 10 may comprise, for example, alkyl bromides, lower molecular weight alkanes (e.g., methane, ethane, etc.), and hydrogen bromide (HBr). The lower molecular weight hydrocarbons generally may be unreacted, excess alkanes that were not fully converted to alkyl bromides in a prior bromination stage, as should be appreciated by those of ordinary skill in the art, with the benefit of this disclosure. The HBr generally may be a byproduct from the bromination of the lower molecular weight alkanes to alkyl bromides, as should also be appreciated by those of ordinary skill in the art, with the benefit of this disclosure. The alkyl bromides present in the feed stream 30 generally may include mono-brominated alkanes (e.g., mono-bromomethane, mono-bromoethane, mono-bromopropane, and the like) and poly-brominated alkanes (e.g., di-bromomethane, di-bromoethane, tri-bromo-ethane, and the like). In some embodiments, the ratio of mono-brominated alkanes to mono-brominated alkanes plus di-bromomethane (RBr/(RBr+DBM)) may be from about 0.6 to about 1.0. In one particular embodiment, this ratio may be from about 0.67 to about 0.9. In some embodiments, it may be desired to limit or otherwise restrict the concentration of di-bromomethane in the feed stream 30 such that the RBr/(RBr+DBM)) ratio is equal to or greater than about 0.9. In some embodiments, a separation unit may be used to reduce the concentration of di-bromomethane in the feed stream 30. Those of ordinary skill in the art, with the benefit of this disclosure, will appreciate that di-bromomethane generally has a higher selectivity to coke formation and, thus, reducing its concentration in the feed stream 30 may reduce the rate of coke formation in the conversion reactor 10 in accordance with embodiments of the present invention.

In the conversion reactor 10, the alkyl bromides in the feed stream 30 may be reacted over a suitable catalyst in the presence of HBr to produce higher molecular weight hydrocarbons and additional HBr. A conversion reactor effluent stream 35, which comprises higher molecular weight hydrocarbons and HBr, may be withdrawn from the conversion reactor 10. The conversion reactor effluent stream 35 may further comprise at least a portion of the excess, unreacted alkanes from the feed stream 30.

In the illustrated embodiment, the conversion reactor 10 further contains heat transfer coils 40 for cooling the conversion reactor 10. Where used, the heat transfer coils 40 generally can recover the heat of reaction from the dehydrohalogenation reactions in the conversion reactor 10, for example, so that catalyst can be maintained in a desirable temperature range. The conversion reactor 10 can be maintained, for example, at a temperature of less than about 500° C. In some embodiments, the conversion reactor 10 can be maintained at a temperature in the range of about 325° C. to about 450° C. and, alternatively, about 375° C. to about 400° C. While heat transfer coils 40 are illustrated, it should be understood that other mechanisms for cooling the conversion reactor 10 can be used in accordance with embodiments of the present invention, such as those depicted in the embodiment shown on FIG. 5 in which a portion of conversion reactor effluent stream 35 is cooled and recycled to the conversion reactor 10. It should be understood that use of a cooling mechanism, such as heat transfer coils 40, is optional and is not employed in some embodiments, for example, in which the temperature increase within the conversion reactor 10 resulting from the heat of reaction is within an acceptable range to minimize coke selectivity and maximize conversion rate such as between about 340° to about 420° C. in the case of a ZSM-5 zeolite catalyst.

The catalyst used in the conversion reactor 10 may be any of a variety of suitable materials for catalyzing the conversion of the alkyl bromides to higher molecular weight hydrocarbons. In the illustrated embodiment, the conversion reactor 10 may comprise a fluidized bed 12 of the catalyst. The fluidized bed 12 of the catalyst may have certain advantages, such as constant removal of coke and a steady selectivity to product composition. In some embodiments, the catalyst may be a granular catalyst having a mean particle size in the range of about 30 microns to about 300 microns. Examples of suitable catalysts include a fairly wide range of materials that have the common functionality of being acidic ion-exchangers and which also contain a synthetic crystalline alumino-silicate oxide framework. The crystalline alumino-silicate may include a microporous or mesoporous crystalline alumino-silicate, but, in certain embodiments, may include a synthetic microporous crystalline zeolite, and, for example, being of the MFI structure such as ZSM-5. Further, the zeolites may be subjected to a chemical and/or hydrothermal de-alumination treatment, which has been found to substantially improve the tolerance of the catalyst to di-bromomethane and reduce the selectivity to coke. In certain embodiments, a portion of the aluminum in the crystalline alumino-silicate oxide framework may be substituted with magnesium, boron, gallium and/or titanium. In certain embodiments, a portion of the silicon in the crystalline alumino-silicate oxide framework may be optionally substituted with phosphorus. The crystalline alumino-silicate catalyst generally may have a significant anionic charge within the crystalline alumino-silicate oxide framework structure which may be balanced, for example, by cations of elements selected from the group H, Li, Na, K or Cs or the group Mg, Ca, Sr or Ba or the group La or Ce. Although zeolitic catalysts may be commonly obtained in a sodium form, a protonic or hydrogen form (via ion-exchange with ammonium hydroxide, and subsequent calcining) is preferred, or a mixed protonic/sodium form may also be used. The zeolite may also be modified by ion exchange with other alkali metal cations, such as Li, K, or Cs, with alkali-earth metal cations, such as Mg, Ca, Sr, or Ba, or with transition metal cations, such as Fe, Ni, Cu, Mn, Pb, V, W or with rare-earth metal cations La or Ce. Such subsequent ion-exchange, may replace the charge-balancing counter-ions, but furthermore may also partially replace ions in the oxide framework resulting in a modification of the crystalline make-up and structure of the oxide framework. Moreover, the crystalline alumino-silicate or substituted crystalline alumino-silicate, in certain embodiments, may be subsequently impregnated with an aqueous solution of a Mg, Ca, Sr, Ba, La or Ce salt. In certain embodiments, the salts may be a halide salt, such as a bromide salt, such as $MgBr_2$, $CeBr_3$ or other solid compound having Lewis acid functionality which has been found to reduce the deactivation rate of the base crystalline alumino-silicate or substituted alumino-silicate catalyst. Optionally, the crystalline alumino-silicate or substituted crystalline alumino-silicate may also contain between about 0.1 weight % to about 1 weight % Pt or about 0.1 weight % to about 5 weight % Pd. Although, such materials are primarily initially crystalline, it should be noted that some crystalline catalysts may undergo some loss of crystallinity either due to initial ion-exchange or impregnation or due to operation at the reaction conditions or during regeneration and hence my also contain significant amorphous character, yet still retain significant, and in some cases improved activity.

Those of ordinary skill in the art should appreciate, with the benefit of this disclosure, that the particular higher molecular weight hydrocarbons produced will be dependent, for example, upon the catalyst employed in the conversion reactor 10, the composition of the alkyl bromides introduced into the conversion reactor 10, and the exact operating parameters employed in the conversion reactor 10. The particular catalyst used in conversion reactor 10 will depend, for example, upon the particular higher molecular weight hydrocarbons that are desired. For example, when higher molecular weight hydrocarbons having primarily C3, C4 and C5+ gasoline-range aromatic compounds and heavier hydrocarbon fractions are desired, a ZSM-5 zeolite catalyst or modified ZSM-5 zeolite catalyst, such as a partially de-aluminated, ion-exchanged ZSM-5 catalyst, may be used. When it is desired to produce higher molecular weight hydrocarbons comprising a mixture of olefins and C5+ products, an X-type or Y-type zeolite catalyst or SAPO zeolite catalyst may be used. An example of a suitable zeolite includes an X-type, such as 10-X, although other zeolites with differing pore sizes and acidities, may be used in embodiments of the present invention.

Those of ordinary skill in the art, with the benefit of this disclosure, should recognize that the catalyst in the conversion reactor 10 will generally undergo a loss of catalytic activity during use. The catalyst is generally considered significantly deactivated when it has accumulated an amount of coke in the range of about 10 to 20 weight % coke (as carbon) or greater. In accordance with present embodiments, the time required for deactivation of the catalyst can vary from a few hours to several days. In some embodiments, the time required for deactivation can vary from about 6 hours to about 48 hours. Some of the factors, which most significantly impact the deactivation rate of the catalyst, include without limitation the composition of the feed (particularly the amount of di-bromomethane present), space velocity, temperature, and type of catalyst.

In general, the catalyst in the conversion reactor 10 becomes deactivated due to the accumulation of "coke," which is generally a carbonaceous material generated on the catalyst during the alkyl bromide conversion. Some of the coke accumulated on the catalyst may be in form of desirable hydrocarbons, such one- and two-ring aromatic compounds, which may be lost if not recovered from the catalyst during catalyst regeneration. In addition, it is believed that some "hydrocarbon pool" intermediates, which are formed in the crystalline cages of the catalyst may be lost if not recovered prior to regeneration. "Hydrocarbon pool" intermediates are believed to be substituted aromatics which undergo addition and are also cleaved into smaller fragments to yield C3+ products.

Figure 2:
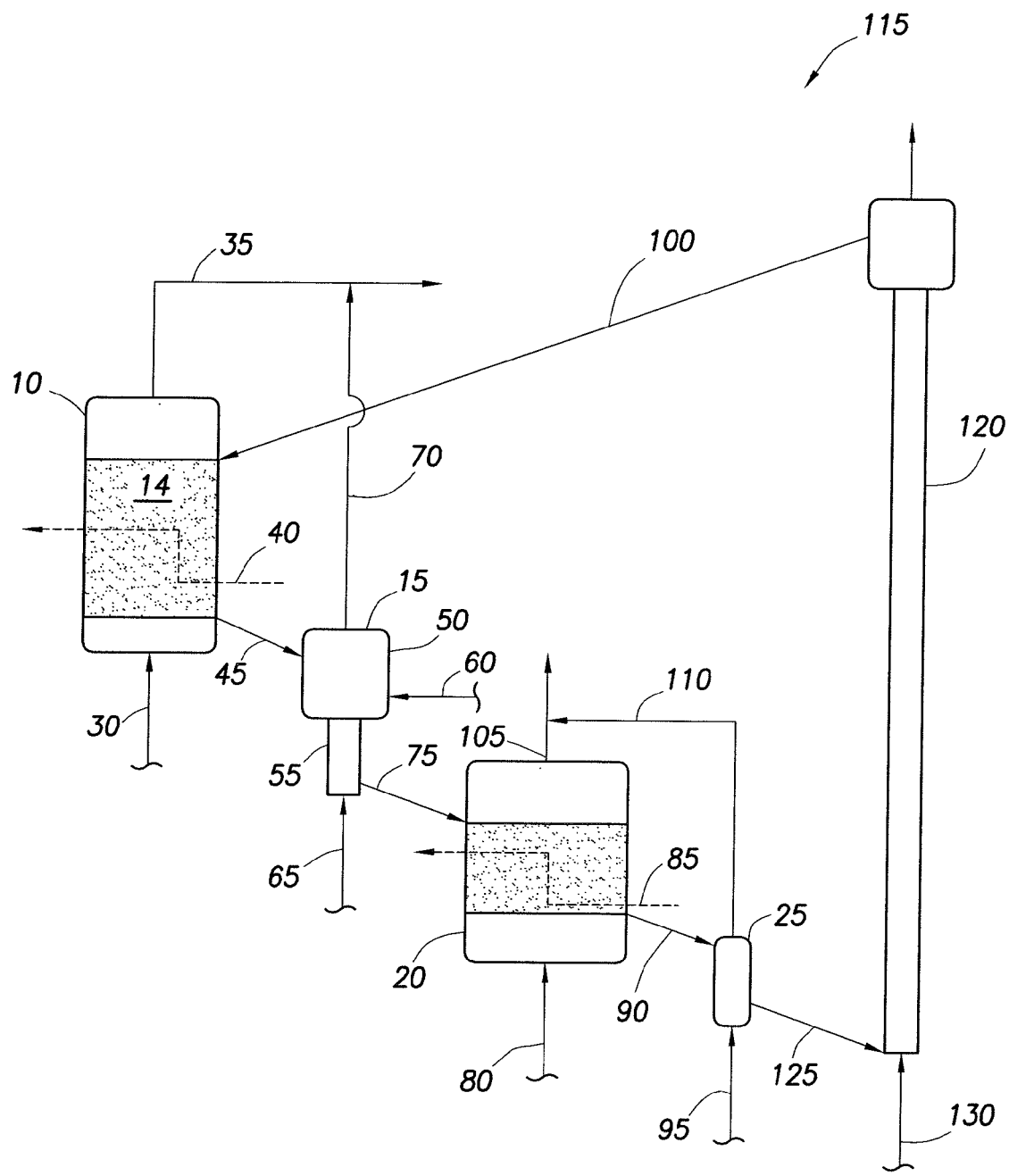
FIG. 2 is a schematic diagram of another embodiment of a reactor-regenerator system of the present invention.

To restore activity, the catalyst can be regenerated in accordance with present embodiments. For regeneration of the deactivated catalyst, a stream 45 comprising at least a portion of deactivated catalyst (e.g., the catalyst with accumulated coke) may be removed from the conversion reactor 10 and introduced into the two-stage stripping unit 15 that comprises an upper stripping stage 50 and a lower stripping stage 55. In an embodiment, the stream 45 can be continuously removed from the conversion reactor 10. In an alternative embodiment, the stream 45 can be intermittently removed from the conversion reactor 10. As illustrated, the stream 45 may be withdrawn, for example, from an upper section of the conversion reactor 10. Alternatively, the stream 45 may be withdrawn from a lower section of the conversion reactor 10, as best seen in FIG. 2. While FIG. 1 illustrates the two-stage stripping unit 15 having only a single vessel, the two-stage stripping unit 15 may include one or more vessels as will be appreciated by those of ordinary skill in the art, with the benefit of this disclosure. For example, the upper and lower stripping stages 50, 55 may be separate vessels in some embodiments.

In the upper stripping stage 50, the deactivated catalyst may be contacted with a stripping gas transported to the two-stage stripping unit 15 via stream 60. The stripping gas generally should remove at least a portion of the C6+ hydrocarbons that may be on the deactivated catalyst. In one embodiment, the stripping gas may comprise a lower molecular weight alkane, such as methane, ethane, propane, or a combination thereof. Alternatively, the stripping gas may comprise a reducing gas, for example, such as hydrogen or a mixture containing hydrogen. It is believed that the reducing gas may have the added beneficial effect of partially saturating the aromatic compounds or hydrocarbon pool intermediates residing in the micro-pores of the deactivated catalyst.

In the lower stripping stage 55, the deactivated catalyst may be contacted with a stream 65 comprising an inert gas, such as nitrogen. The inert gas generally should remove at least a portion of the stripping gas from the deactivated catalyst, minimizing its loss thereof to oxidation in the regeneration reactor 20. The residence time of the deactivated catalyst in the upper stripping stage 50 generally may be greater than the residence time of the deactivated catalyst in the lower stripping stage 55, for example, to give sufficient time to desorb a significant portion of the adsorbed stripping gas. In some embodiments, the residence time in the upper stripping stage 50 may be in the range of about 5 minutes to about 120 minutes while the residence time in the lower stripping stage 55 may be in the range of about 1 minute to about 15 minutes.

A stream 70 comprising the C6+ hydrocarbons removed from the deactivated catalyst may be withdrawn from the two-stage stripping unit 15 and combined with the conversion reactor effluent stream 35. In this manner, at least a portion of the C6+ hydrocarbons that were adsorbed onto the catalyst in the conversion rector 10 may be recovered, thus minimizing carbon loss from the catalyst. The C6+ hydrocarbons may be in the form of, for example, multi-ring aromatic compounds and/or hydrocarbon pool intermediates. The stream 70 of the C6+ hydrocarbons may further comprise at least portion of the stripping and inert gases introduced into the two-stage stripping unit 15 via stream 60 and stream 65, respectively.

Another stream 75 comprising the stripped, deactivated catalyst may be withdrawn from the first stripping unit 15 and introduced into the regeneration reactor 20 for contact with oxygen to regenerate at least a portion of the catalyst. In some embodiments, the regeneration reactor 20 may contain a fluidized bed 22 of the catalyst. An oxygen-containing gas stream 80 may be fed to the regeneration reactor 20. In the illustrated embodiment, the oxygen-containing gas stream 80 is fed at or near the bottom of the regeneration reactor 20. The oxygen-containing gas stream 80 may include oxygen and/or air, for example. In the regeneration reactor 20, oxygen from stream 80 reacts with the coke deposits on the deactivated catalyst to yield carbon oxides (e.g., $CO$, $CO_2$) and steam, thus removing at least a portion of the coke deposits on the deactivated catalyst by oxidation. In this manner, the deactivated catalyst can be regenerated for reuse in the conversion reactor 10. Surprisingly, it has been discovered that embodiments of the catalyst can still be active with up to about 20 weight % coke on the catalyst. Accordingly, in some embodiments, the catalyst can be regenerated in the regeneration reactor 20 to yield a regenerated catalyst having less than about 1 weight % to about 10 weight % coke on the catalyst. In some embodiments, the catalyst can be fully regenerated, which ensures the highest level of catalyst activity. As used herein, a catalyst is considered fully regenerated if the amount of coke on the catalyst is less than about 0.1 weight %. However, it has been discovered that the coke formation rate in the conversion reactor 10 may be reduced if some coke is left on the catalyst as the most active coke-forming sites on the catalyst are also the most easily deactivated leading to a partial self-passivating effect. Accordingly, it may be desirable to leave some coke on the catalyst in accordance with embodiments of the present invention. For example, the catalyst can be regenerated in the regeneration reactor 20 to yield a regenerated catalyst having about 2 weight % to about 10 weight % coke on the catalyst and, alternatively, from about 2 weight % to about 5 weight % coke on the catalyst.

The regeneration reactor 20 generally may operate at a temperature in the range of about 450° C. to about 650° C. and a pressure in the range of about 1 atmosphere to about 50 atmospheres. In accordance with embodiments of the present invention, it can be important to keep the temperature of the catalyst below about 650° C. and more preferably to keep the catalyst in the range of about 500° to about 550° C. In some embodiments, this may be achieved by dilution of the oxygen or air with nitrogen (such as by recycling a portion of the regeneration off gas). In some embodiments, the regeneration reactor 20 may include heat transfer coils 85 for recovering heat from the exothermic, oxidative reactions occurring in the regeneration reactor 20. The regeneration reactor 20 may be maintained, for example, at a temperature of less than about 650° C. and, alternatively, below about 550° C. As illustrated, the heat transfer coils 85 may be disposed in the fluidized bed 22 of the catalyst. Maintenance of temperature below these levels may be desirable, in accordance with embodiments of the present invention, to prevent high-temperature and/or hydrothermal degradation of the catalyst that could occur at higher temperatures in some embodiments. While heat transfer coils 85 are illustrated, it should be understood that other mechanisms for cooling the regeneration reactor 20 can be used in accordance with embodiments of the present invention.

A stream 90 comprising the regenerated catalyst may be withdrawn from the regeneration reactor 20 and introduced into the second stripping unit 25. In the second stripping unit 25, the regenerated catalyst may be contacted with an inert gas stream 95, which may be fed to the bottom of the second stripping unit 25 as seen in FIG. 1. The inert gas stream 95 may comprise an inert gas, such as nitrogen, among others. The inert gas generally should remove residual oxygen, carbon oxides, and/or steam that may be retained on the regenerated catalyst. For example, the inert gas may displace residual oxygen, carbon oxides, and/or steam that may be retained in the interstitial spaces between catalyst granules or adsorbed on the catalyst. The inert gas used in second stripping unit 25 may be the same or different than the inert gas used in the lower stripping stage 55. In the illustrated embodiment, the second stripping unit 25 has a single stripping stage. A catalyst feed stream 100 comprising at least a portion of the regenerated catalyst may be withdrawn from the second stripping unit 25 and introduced into the conversion reactor 10. As illustrated, the catalyst feed stream 100 may introduce the regenerated catalyst into a lower section of the conversion reactor 10. Alternatively, the catalyst feed stream 100 may be introduced into an upper section of the conversion reactor 10, as best seen in FIG. 2.

The residual air or oxygen from the oxygen-containing gas stream 80 may be withdrawn from the regeneration reactor 20 via stream 105. Carbon oxides and/or steam generated in the regeneration reactor 20 by the oxidation of the coke on the deactivated catalyst may also be removed via stream 105. As illustrated, stream 105 may be combined with stream 110 from the second stripping unit 25. In present embodiments, the stream 110 may comprise the residual inert gas as well as oxygen, carbon oxides, and/or steam removed from the regenerated catalyst in the second stripping unit 25. As the combined streams from the regeneration reactor 20 and the second stripping unit 25 may contain small amounts of bromine-containing species, as well as excess unreacted oxygen, this combined stream may be directed to a unit for bromine recovery (e.g., HBr oxidation unit 265 on FIG. 6), wherein the bromine-containing species may be converted to elemental bromine and recovered for re-use.

Referring now to FIG. 2, a first moving-bed reactor system 115 for converting alkyl bromides in the feed stream 30 to higher molecular hydrocarbons is illustrated in accordance with embodiments of the present invention. The moving-bed reactor system 115 differs from the rector-regenerator system 5 shown on FIG. 1, in that the illustrated embodiment includes a moving bed 14 of a pelletized catalyst, which may be of any suitable shape, such as spherical. In some embodiments, the pelletized catalyst may have a mean particle size in the range of about 1 millimeter to about 10 millimeters. Examples of suitable pelletized catalyst include the catalysts described above with respect to FIG. 1. As illustrated, the regenerated catalyst may be introduced at or near the top of the conversion reactor 10 via catalyst feed stream 100. Those of ordinary skill will recognize that the introduction of the regenerated catalyst to the conversion reactor 10 may be intermittent or continuous as desired for a particular application. Within the conversion reactor 10, the catalyst moves downward, concurrently to the upward flow of vapor within the conversion reactor 10. The downward flow of the catalyst may be intermittent or continuous as will be recognized by those of ordinary skill with the benefit of this disclosure. A stream 45 comprising deactivated catalyst may be removed from at or near the bottom of the conversion reactor 10 and introduced into the two-stage stripping unit 15. The other process components depicted in FIG. 2, including the two-stage stripping unit 15, regeneration reactor 20, and second stripping unit 25, may be substantially similar in function and operation as the analogous components described above with respect to FIG. 1 with the exception of riser 120, which lifts the regenerated catalyst for introduction at or near the top of the conversion reactor 10. In the illustrated embodiment, the riser 120 receives a stream 125 comprising the regenerated catalyst from the second stripping unit 25 and uses a gas stream 130 to lift the regenerated catalyst so that catalyst feed stream 100 can be introduced at or near the top of the conversion reactor 10. The gas stream 130 may comprise an inert gas as will be apparent to those of ordinary skill in the art with the benefit of this disclosure. In an alternative embodiment (not shown), a mechanical conveying device may be used in the riser 120 for mechanically lifting the regenerated catalyst and conveying it to the conversion reactor 10.

Figure 3:
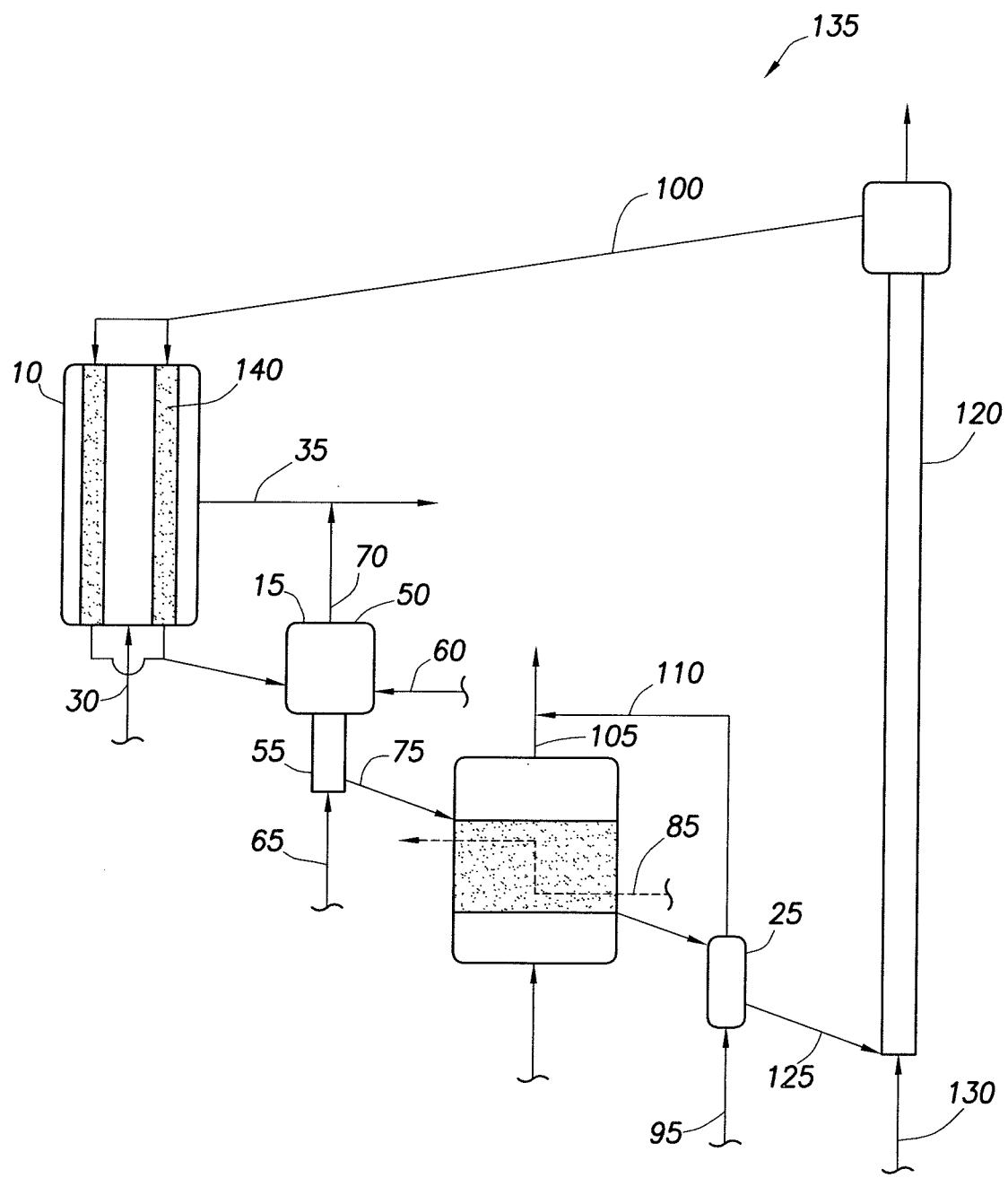
FIG. 3 is a schematic diagram of yet another embodiment of a reactor-regenerator system of the present invention.

FIG. 3 illustrates an alternative moving-bed reactor system 135 in accordance with alternative embodiments of the present invention. In the illustrated embodiment, the alternative moving-bed reactor system 135 is substantially similar in function and operation to the embodiment described above with respect to FIG. 2, except that the catalyst is arranged in an annular bed 140. In the illustrated embodiment, the reactants fed to the reactor in feed stream 30 pass radially through the downward flowing catalyst in the annular bed 140. While inward-to-outward reactant flow across the annular bed 140 is depicted in FIG. 3, it may be advantageous for reactants to flow outward to inward in alternative embodiments of the present invention.

Figure 4:
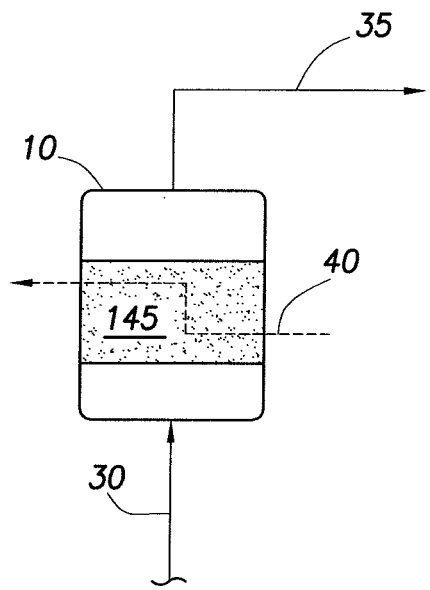
FIG. 4 is a schematic diagram of one embodiment for cooling a conversion reactor of the present invention.

FIG. 4 illustrates one technique for cooling the conversion reactor 10 in accordance with embodiments of the present invention. As illustrated, the conversion reactor 10 may contain heat transfer coils 40 disposed in a catalyst bed 145, which may be, for example, a fluidized- or moving-bed as previously discussed. A suitable heat transfer fluid, such as boiling water, may be passed through the heat transfer coils 40 for recovering the heat of reaction from the dehydrohalogenation reaction occurring in the conversion reactor 10.

Figure 5:
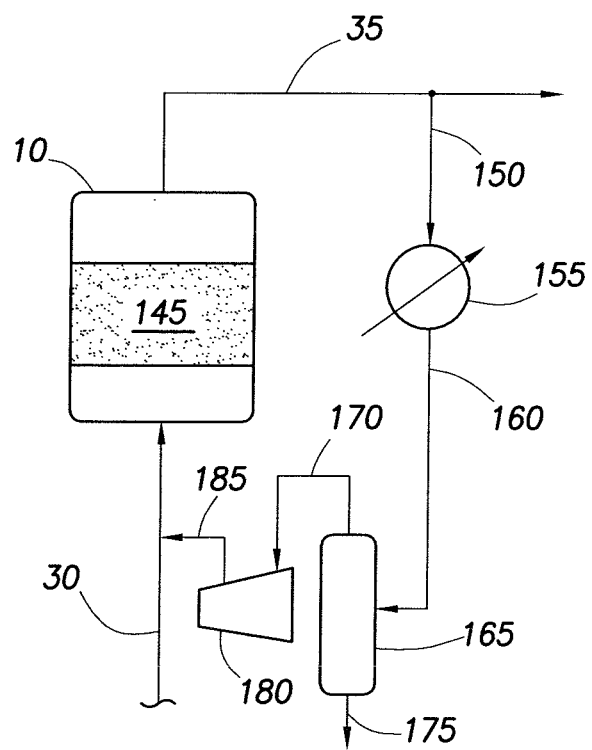
FIG. 5 is a schematic diagram of another embodiment for cooling a conversion reactor of the present invention.

FIG. 5 illustrates another technique for cooling the conversion reactor 10 in accordance with embodiments of the present invention. In the illustrated embodiment, a slipstream 150 of the conversion reactor effluent stream 35 is cooled in heat exchanger 155. In one particular embodiment, the slipstream 150 may contain lower molecular weight alkanes, such as methane, ethane, and/or propane. The cooled slipstream 160, which may have been partially condensed, can be sent to separator 165 for vapor-liquid phase separation. In the separator 165, the cooled slipstream 160 may be separated into a gas stream 170 and a liquid stream 175. The gas stream 170 may be fed to compressor 180 that compresses the gas stream 170 and delivers a compressed gas stream 185 to the conversion reactor 10. As illustrated, the compressed gas stream 185 may be combined with the feed stream 30 prior to introduction into the conversion reactor 10, thus cooling the alkyl bromides contained in the feed stream 30. In addition to cooling the conversion reactor 10, it has been found that the presence of alkanes, such as propane, may serve as hydrogen donors, thus potentially lowering the selectivity of the alkyl bromide conversion to coke.

In accordance with embodiments of the present invention, the reactor-regenerator systems described above with respect to FIGS. 1-5 for the conversion of alkyl bromides to higher molecular weight hydrocarbons may be used in a bromine-based process for the production of higher molecular weight hydrocarbons from lower molecular weight alkanes. For example, a stream of lower molecular weight hydrocarbons may be reacted with bromine from a suitable bromine source to produce alkyl bromides. These alkyl bromides may then be reacted over suitable catalyst so as to form higher molecular weight hydrocarbons. The above-described reactor-regenerator systems may be used for this alkyl bromides conversion.

Figure 6:
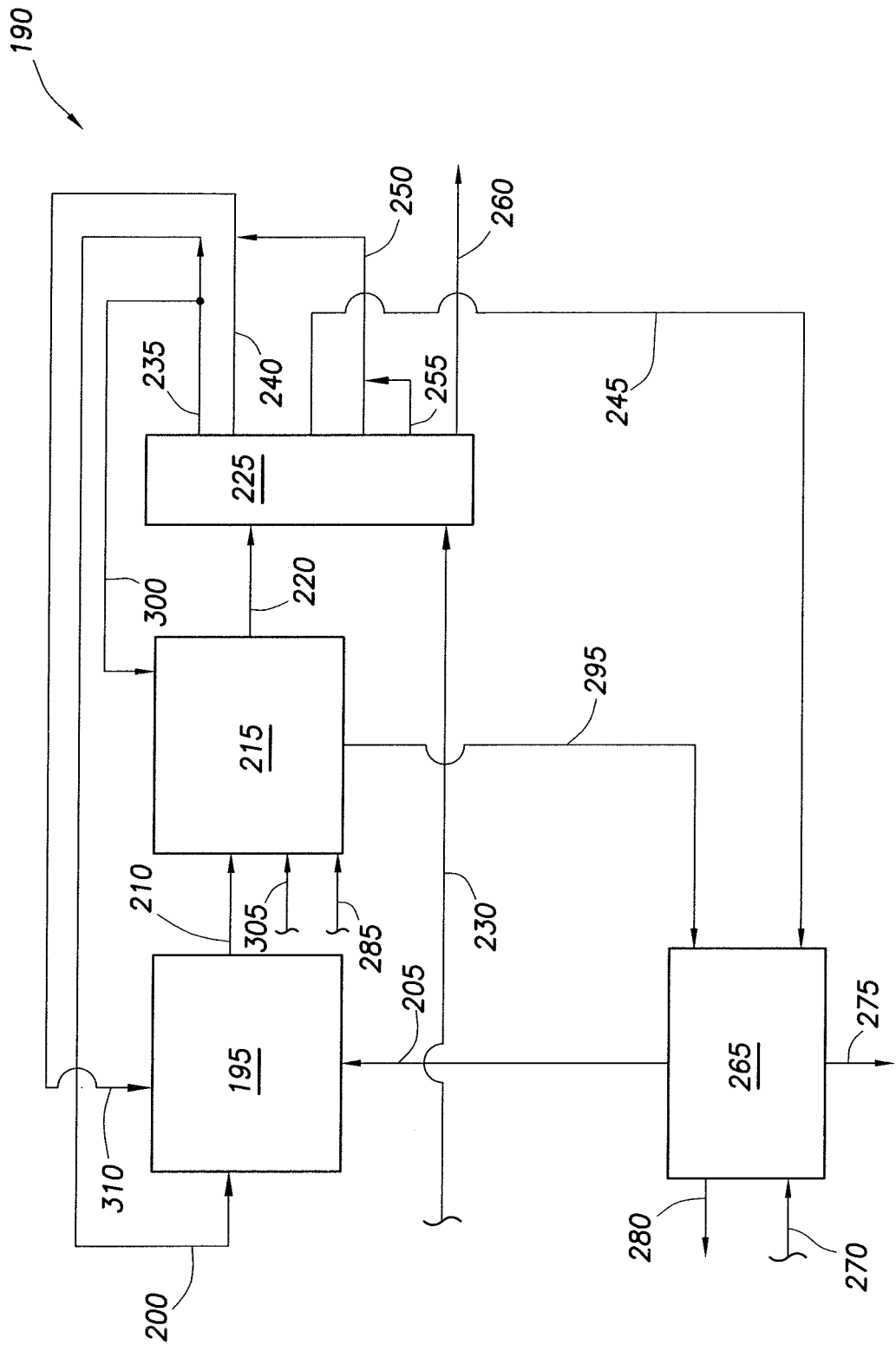
FIG. 6 is a schematic diagram of one embodiment of a process for producing higher molecular weight hydrocarbons.

A block flow diagram generally depicting an embodiment of a process 190 for producing higher molecular weight hydrocarbons from lower molecular weight alkanes is illustrated in FIG. 6. As illustrated by FIG. 6, the process 190 may include a bromination stage 195 in which a gas stream 200 comprised primarily of methane, for example, derived from a mixture of feed gas plus a recycled gas stream, may react with bromine from bromine stream 205 to produce alkyl bromides and HBr. In some embodiments, the bromine may be a substantially dry bromine vapor. In some embodiments, the bromination stage 195 may include separate and parallel bromination of methane and C2+ alkanes contained in stream 310. In some embodiments, the bromination stage 195 further may include separate and parallel bromination of C2 alkanes and C3+ alkanes. A stream 210 comprising the resultant alkyl bromides may be withdrawn from the bromination stage 195 and fed into a circulating catalyst reactor-regenerator system 215. In the circulating catalyst reactor-regenerator system 215, the alkyl bromides may be reacted over a suitable catalyst in the presence of HBr to produce higher molecular weight hydrocarbons. In addition, as described above with respect to FIGS. 1-5, the catalyst in the circulating catalyst reactor-regenerator system 215 may be regenerated by a process that includes, for example, a two-stage stripping unit 15, a regeneration reactor 20, and a second stripping unit 25.

A reactor effluent stream 220 may be withdrawn from the reactor-regenerator system 215 and introduced to a hydrogen bromide ("HBr") removal and product recovery unit 225. In some embodiments, the reactor effluent stream 220 may comprise unreacted hydrocarbons (e.g., C1-C3 hydrocarbons), higher molecular weight hydrocarbons produced by the reaction of alkyl bromides over a suitable catalyst in reactor-regenerator system 215, and HBr. As illustrated, a feed gas stream 230 comprising lower molecular weight hydrocarbons, such as natural gas, can also be introduced to the product recovery unit 225.

In the HBr removal and product recovery unit 225, the HBr generated in the bromination stage 195 and the reactor-regenerator system 215 may be separated from the hydrocarbon components. As illustrated, separation of the HBr may be combined with separation of the hydrocarbon components into their respective fractions for product recovery and recycle. For example, the HBr removal and product recovery unit 225 may separate the respective feeds into a methane stream 235, an ethane stream 240, an HBr stream 245, a propane stream 250, a butane stream 255, and a liquid product stream 260. Any suitable technique may be used for separation of the HBr and hydrocarbons in the HBr removal and product recovery unit 225, including, for example, cryogenic separation, fractionation, extractive distillation, or a refrigerated lean-oil process, among others, as should be evident to those of ordinary skill in the art with the benefit of this disclosure. In the illustrated embodiment, a portion of the methane stream 235 is recycled to bromination stage 195. The ethane stream 240, propane stream 250, and butane stream 255 may be combined into stream 310 and recycled to the bromination stage 195 as illustrated by FIG. 6, for example. While not illustrated, stream 240 and a mixture of streams 250 and 255 may be separately recycled for bromination in two separate C2 and C3+ bromination reactors. HBr stream 245 withdrawn from the HBr removal and product recovery unit 225 may be fed to the HBr oxidation unit 265 for recovery of elemental bromine. Liquid product stream 260 comprising C4+ hydrocarbons may also be withdrawn from the HBr removal and product recovery unit 225.

In the HBr oxidation unit 265, the separated HBr in HBr stream 245 may be oxidized with oxygen from stream 270 to produce elemental bromine and water. Stream 270 may comprise, for example, oxygen, air, or any other suitable source of oxygen. The water produced from oxidation of the HBr and coke may be withdrawn via first water stream 275. The elemental bromine may be withdrawn via bromine stream 205. Oxygen-depleted gas 280 may also be withdrawn from the HBr oxidation unit 265.

A portion 300 of the methane stream 235 recycled to the bromination stage 195 may also be fed to reactor-regenerator system 215 and used to strip the catalyst of heavier hydrocarbons. An inert gas stream 305, such as nitrogen, may also be fed to reactor-regenerator system 215 and used to displace methane from the catalyst prior to the circulated catalyst being oxidatively regenerated. An oxygen-containing stream 285 may also be introduced to reactor-regenerator system 215 for oxidative regeneration of the catalyst. The catalyst regeneration off-gas 295, leaving the reactor-regenerator system 215, which should comprise carbon oxides and which may also contain bromine and HBr may be routed to the HBr oxidation unit 265.

While FIG. 6 illustrates separation of the HBr while separating the hydrocarbon components into their respective fractions for product recovery and recycle, it should be understood that other suitable techniques for HBr separation and product recovery may also be used in accordance with embodiments of the present invention. For example, some embodiments may separate the HBr prior to separation of the hydrocarbon components into their respective fractions. Non-limiting examples of techniques for HBr separation include absorption of HBr into an aqueous solution, adsorption of HBr on a metal oxide, or electrolysis of the HBr to form elemental bromine. The hydrocarbons may then be fed to a product recovery unit wherein any suitable method of product recovery may be employed, including refrigerated condensation, cryogenic separation, or circulating absorption oil or some other solvent. In some embodiments, the hydrocarbons may first be dehydrated by a technique, such as solid-bed desiccant adsorption, prior to separation into their desired fractions.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. All numbers and ranges disclosed above may vary by some amount. Whenever a numerical range with a lower limit and an upper limit is disclosed, any number and any included range falling within the range are specifically disclosed.

What is claimed is:

1. A process comprising:
   reacting at least alkyl bromides over a catalyst in at least one conversion reactor to produce at least an effluent stream comprising higher molecular weight hydrocarbons and hydrogen bromide;
   removing a portion of the catalyst from the conversion reactor;
   contacting the portion of the catalyst with a stripping gas to displace hydrocarbons from the portion of the catalyst;
   contacting the portion of the catalyst with a first inert gas;
   contacting the portion the catalyst with oxygen to form a regenerated catalyst by removal of coke;
   contacting the regenerated catalyst with a second inert gas which is nitrogen; and
   introducing at least a portion of the regenerated catalyst into the conversion reactor.

2. The process of claim 1 wherein the catalyst comprises a crystalline alumino-silicate framework, and wherein the higher molecular weight hydrocarbons comprise hydrocarbons having six or more carbon atoms and the alkyl bromides comprise bromomethane.

3. The process of claim 1 wherein the alkyl bromides have a ratio of mono-brominated alkanes to mono-brominated alkanes plus di-brominated alkanes of equal to or greater than about 0.9.

4. The process of claim 1 wherein the portion of the catalyst removed from the conversion reactor comprises coke in an amount of equal to or greater than about 10 weight %.

5. The process of claim 1 wherein the stripping gas comprises at least one alkane selected from the group consisting of methane, ethane, propane, and any combination thereof.

6. The process of claim 1 wherein the stripping gas comprises hydrogen.

7. The process of claim 1 wherein the regenerated catalyst comprises coke in an amount of about 2 weight % to about 10 weight %.

8. The process of claim 1 wherein the regenerated catalyst comprise coke in an amount of less than about 0.1 weight %.

9. The process of claim 1 further comprising combining the stripping gas comprising the displaced hydrocarbons with the effluent stream from the conversion reactor, wherein the displaced hydrocarbons comprise hydrocarbons comprising six or more carbon atoms.

10. The process of claim 1:
    wherein the stripping gas contacts the portion of the catalyst in an upper stripping stage;
    wherein the first inert gas contacts the portion of the catalyst in a lower stripping stage; and
    wherein a residence time of the catalyst in the upper stripping stage is greater than a residence time of the portion of the catalyst in the lower stripping stage.

11. The process of claim 1 wherein the contacting the portion the catalyst with oxygen is at a temperature of about 450° C. to about 650° C.

12. The process of claim 1 wherein the conversion reactor comprises a moving bed of the catalyst, the catalyst having a particle size of about 1 millimeter to about 10 millimeters, and wherein the regenerated catalyst is introduced at or near a top of the conversion reactor.

13. The process of claim 12 wherein the catalyst is arranged in the conversion reactor in an annular bed.

14. The process of claim 1 further comprising:
    cooling a slipstream of the effluent stream;
    separating a gas stream from the cooled effluent stream;
    combining the gas stream with the alkyl bromides; and
    introducing the gas stream and the alkyl bromides to the conversion reactor.

15. The process of claim 1 further comprising:
    removing hydrogen bromide from effluent stream;
    oxidizing the hydrogen bromide to produce elemental bromine and water; and
    reacting the elemental bromine with lower molecular alkanes to produce additional alkyl bromides that are introduced into the conversion reactor.

16. The process of claim 15 wherein the removing the hydrogen bromide comprises separating the effluent stream into at least a methane stream, an ethane stream, a hydrogen bromide stream, a butane stream, and a liquid product stream, the liquid product stream comprising hydrocarbons having four or more hydrocarbons.

17. A process comprising:
    reacting at least bromomethane over a crystalline alumino-silicate catalyst in at least one conversion reactor to produce at least an effluent stream comprising higher molecular weight hydrocarbons and hydrogen bromide;
    introducing a portion of the catalyst from the conversion reactor into a two-stage stripping unit;
    introducing a stripping gas into an upper stage of the two-stage stripping unit to displace hydrocarbons from the portion of the catalyst, the hydrocarbons comprising hydrocarbons having six or more carbon atoms;

introducing a first inert gas into a lower stage of the two-stage stripping unit to remove a quantity of the stripping gas from the portion of the catalyst;

introducing the portion of the catalyst from the two-stage stripping unit into a regeneration reactor to form a regenerated catalyst, wherein the portion of the catalyst is contacted with an oxygen-containing stream for coke removal; and introducing at least a portion of the regenerated catalyst into the conversion reactor.

18. The process of claim 17 wherein the portion of the catalyst removed from the conversion reactor comprises coke in an amount of equal to or greater than about 10 weight %, and wherein the regenerated catalyst comprise coke in an amount of about 2 weight % to about 10 weight %.

19. The process of claim 17 further comprising:

removing hydrogen bromide from the effluent stream in a hydrogen bromide removal unit;

oxidizing the hydrogen bromide to produce elemental bromine and water; and reacting the elemental bromine with lower molecular alkanes to produce additional bromomethane that are introduced into the conversion reactor, the lower molecular alkanes comprising recycled methane and feed methane that was fed to the hydrogen bromide removal unit.

\* \* \* \* \*